US011253005B2

(12) United States Patent
Marubashi

(10) Patent No.: US 11,253,005 B2
(45) Date of Patent: Feb. 22, 2022

(54) CONTROL DEVICE OF AEROSOL INHALER

(71) Applicant: JAPAN TOBACCO INC., Tokyo (JP)

(72) Inventor: Keiji Marubashi, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 17/082,055

(22) Filed: Oct. 28, 2020

(65) Prior Publication Data
US 2021/0120884 A1 Apr. 29, 2021

(30) Foreign Application Priority Data
Oct. 28, 2019 (JP) .............................. JP2019-195600

(51) Int. Cl.
A24F 40/57 (2020.01)
A24F 40/51 (2020.01)

(52) U.S. Cl.
CPC .............. A24F 40/57 (2020.01); A24F 40/51 (2020.01)

(58) Field of Classification Search
CPC ........... H02J 7/007; A24F 40/50; A24F 50/57; A24F 40/51
See application file for complete search history.

(56) References Cited

U.S. PATENT DOCUMENTS

| 2006/0047368 | A1* | 3/2006 | Maharajh | A61M 11/042 700/283 |
| 2013/0319435 | A1 | 12/2013 | Flick | |
| 2014/0270727 | A1* | 9/2014 | Ampolini | F24H 9/0005 392/387 |
| 2016/0143359 | A1* | 5/2016 | Xiang | A24F 40/53 392/387 |
| 2016/0360786 | A1 | 12/2016 | Bellinger et al. | |
| 2017/0013879 | A1 | 1/2017 | Fresbee et al. | |
| 2019/0082736 | A1 | 3/2019 | Sur | |
| 2020/0260793 | A1 | 8/2020 | Yamada et al. | |
| 2020/0352248 | A1* | 11/2020 | Yamada | G01K 7/206 |
| 2021/0038836 | A1* | 2/2021 | Rogan | A61M 15/06 |

FOREIGN PATENT DOCUMENTS

| CN | 204742630 U | 11/2015 |
| JP | 2014-501107 A | 1/2014 |
| WO | 2018/122412 A1 | 7/2018 |

(Continued)

OTHER PUBLICATIONS

Office Action received for Japanese Patent Application No. 2019-195600, dated Feb. 12, 2020, 19 pages including English Translation.

(Continued)

Primary Examiner — Anthony Calandra
(74) Attorney, Agent, or Firm — Xsensus LLP

(57) ABSTRACT

A control device of an aerosol inhaler includes a load heating an aerosol generation source, in which a temperature and an electric resistance value of the load are correlated. The control device includes: a voltage sensor configured to output a voltage value applied to the load; a constant current circuit configured to output a constant current to the load; and a control circuit configured to acquire the electric resistance value of the load or the temperature of the load based on output of the voltage sensor and the constant current.

5 Claims, 15 Drawing Sheets

(56) References Cited

FOREIGN PATENT DOCUMENTS

WO   2019/082264 A1   5/2019
WO   2019146062 A1   8/2019

OTHER PUBLICATIONS

Decision to Grant a Patent received for Japanese Patent Application No. 2019-195600, dated Aug. 4, 2020, 5 pages including English Translation.
Partial European search report dated Mar. 19, 2021, in corresponding European patent Application No. 20204364.2, 14 pages.
European Search Report dated Jun. 21, 2021 in corresponding European patent Application No. 20204364.2.
European Search Report dated Jul. 30, 2021 in European Application No. 20 204 364.2.

* cited by examiner

CONTROL DEVICE OF AEROSOL INHALER

CROSS-REFERENCE TO RELATED APPLICATIONS

This application is based on and claims priority under 35 USC 119 from Japanese Patent Application No. 2019-195600 filed on Oct. 28, 2019, the contents of which are incorporated herein by reference.

TECHNICAL FIELD

The present disclosure relates to a control device and a control method of an aerosol inhaler and a control program of the control device.

BACKGROUND ART

In an aerosol inhaler, an electric resistance value and a temperature of a load (for example, a heater) configured to atomize an aerosol source are used for various controls. As a technique for acquiring the electric resistance value or the like of such a load, Patent Literature 1 (WO2019/082264) describes a technique in which a constant voltage is applied to a load by a constant voltage output circuit (for example, a DC/DC converter) and an electric resistance value of the load is obtained from the constant voltage and a current value flowing through the load. Patent Literature 2 (JP-T-2014-501107) describes a technique in which a voltage dividing circuit is formed by a heater and a resistor, a voltage applied only to the resistor and a voltage applied to both the heater and the resistor are measured, and an electric resistance value of a load is obtained from the two voltages.

However, in the techniques described in Patent Literature 1 and 2, in order to obtain the electric resistance value and the temperature of the load, a circuit of an aerosol inhaler may be enlarged or complicated.

For example, in the technique described in Patent Literature 1, the constant voltage output circuit, which tends to be large in circuit scale, is required. Moreover, in the technique described in Patent Literature 2, it is necessary to measure at least two voltages in the voltage dividing circuit where the load is provided, and two voltage sensors are thus required.

The present disclosure provides a control device of an aerosol inhaler, which can highly accurately acquire the electric resistance value or the temperature of the load configured to atomize the aerosol source with a simple configuration, and a control method and a control program of the control device.

SUMMARY

In a first aspect of the disclosure, a control device of an aerosol inhaler includes a load heating an aerosol generation source, in which a temperature and an electric resistance value of the load are correlated. The control device includes: a voltage sensor configured to output a voltage value applied to the load; a constant current circuit configured to output a constant current to the load; and a control circuit configured to acquire the electric resistance value of the load or the temperature of the load based on output of the voltage sensor and the constant current.

In a second aspect of the disclosure, a control method of an aerosol inhaler includes a load heating an aerosol generation source, in which a temperature and an electric resistance value of the load are correlated. The control method includes: first acquiring a voltage value applied to the load; and second acquiring the electric resistance value of the load or the temperature of the load based on the voltage value applied to the load acquired in the first acquiring and a current value of a constant current output to the load.

In a third aspect of the disclosure, a control device of an aerosol inhaler includes a load heating an aerosol generation source, in which a temperature and an electric resistance value of the load are correlated. The control device includes: a sensor configured to output an electric variable of the load; and a control circuit configured to acquire the electric resistance value of the load or the temperature of the load based only on output of the sensor and a constant.

In a fourth aspect of the disclosure, a control method of an aerosol inhaler includes a load heating an aerosol generation source, in which a temperature and an electric resistance value of the load are correlated. The control method includes: first acquiring an electric variable of the load; and second acquiring the electric resistance value of the load or the temperature of the load based only on the electric variable of the load acquired in the first acquiring and a constant.

In a fifth aspect of the disclosure, a control program is configured to cause a computer to execute the control method according to the second aspect or the fourth aspect.

DESCRIPTION OF EMBODIMENTS

Figure 1:
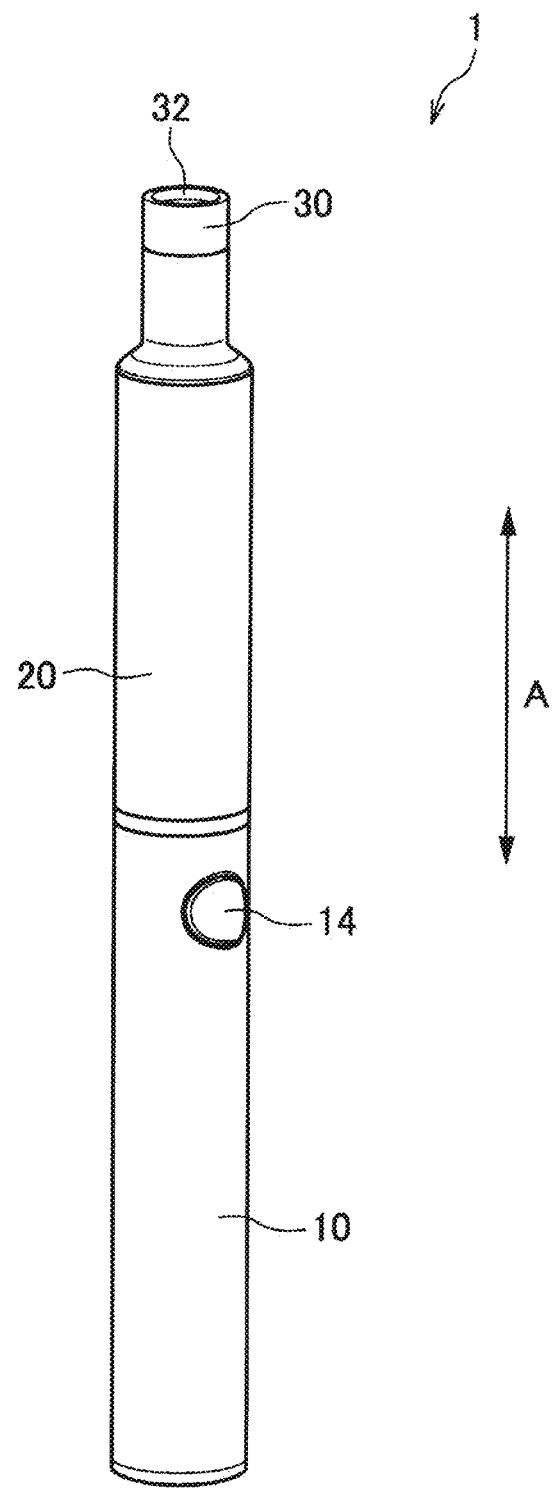
FIG. 1 is a perspective view of an aerosol inhaler equipped with a power supply unit of one embodiment of the present disclosure.
Figure 2:
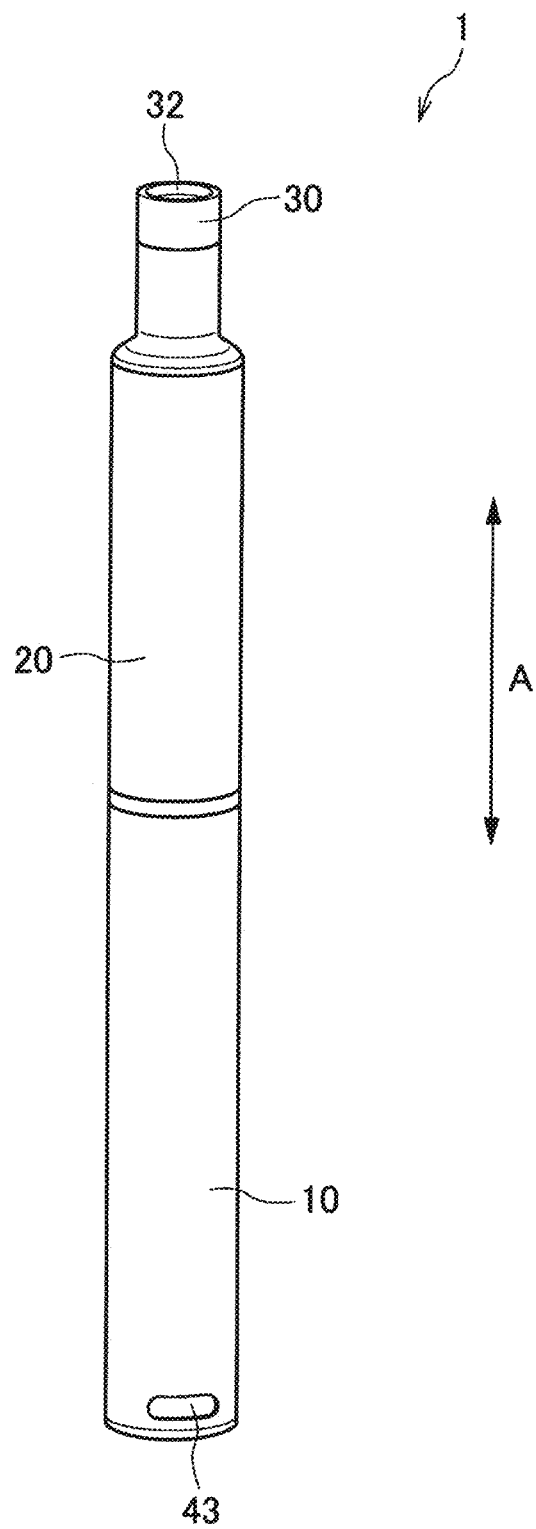
FIG. 2 is another perspective view of the aerosol inhaler of FIG. 1.

Hereinafter, one embodiment of the present disclosure will be described. The embodiment described below is an example in a case where a control device of an aerosol inhaler and an aerosol inhaler of the present disclosure are applied to an aerosol inhaler power supply unit and an aerosol inhaler which includes the power supply unit. First, the aerosol inhaler will be described with reference to FIGS. 1 and 2.

(Aerosol Inhaler)

An aerosol inhaler 1 is an instrument for inhaling a flavored aerosol without burning, and has a rod shape extending along a predetermined direction (hereinafter referred to as a longitudinal direction X).

In the aerosol inhaler 1, a power supply unit 10, a first cartridge 20, and a second cartridge 30 are provided in such an order along the longitudinal direction X. The first cartridge 20 is attachable to and detachable from the power supply unit 10. The second cartridge 30 is attachable to and detachable from the first cartridge 20. In other words, the first cartridge 20 and the second cartridge 30 are replaceable.

(Power Supply Unit)

The power supply unit 10 of the present embodiment is an example of a control device of the present disclosure. As illustrated in FIGS. 3, 4, 5, and 6, a power supply 12, a charger 13, a control circuit 50, and various sensors, such as an intake sensor 15, are accommodated inside a cylindrical power supply unit case 11. The power supply 12 is a rechargeable secondary battery, an electric double layer capacitor, or the like, and is preferably a lithium ion secondary battery. An electrolyte of the power supply 12 may be constituted by one of a gel electrolyte, an electrolytic solution, a solid electrolyte, an ionic liquid, or a combination thereof. The control circuit 50 is, for example, a micro controller unit (MCU).

Figure 4:
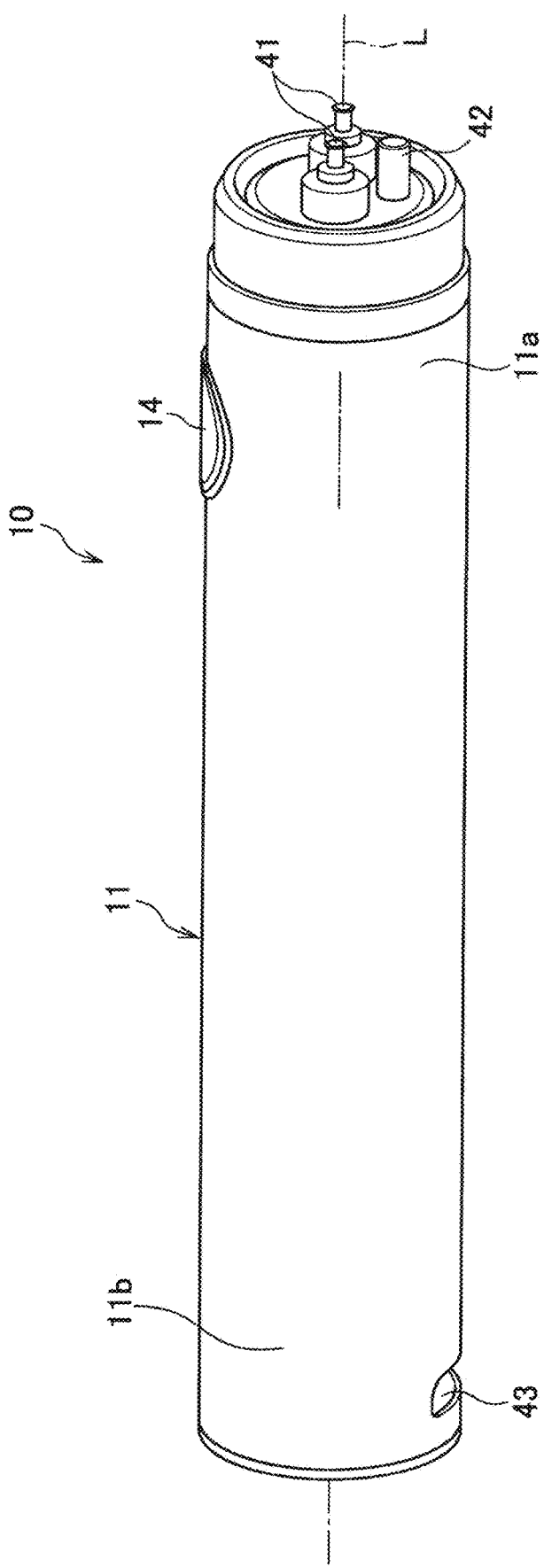
FIG. 4 is a perspective view of the power supply unit of the aerosol inhaler of FIG. 1.

As illustrated in FIG. 4, a discharge terminal 41 is provided on a top portion 11a located on one end side (side of the first cartridge 20) of the power supply unit case 11 in the longitudinal direction X. The discharge terminal 41 protrudes from an upper surface of the top portion 11a toward the first cartridge 20, and is configured to be electrically connectable to a load 21 of the first cartridge 20.

An air supply unit 42 configured to supply air to the load 21 of the first cartridge 20 is provided on the upper surface of the top portion 11a in the vicinity of the discharge terminal 41.

A charge terminal 43 that is electrically connectable to an external power supply (not illustrated) capable of charging the power supply 12 is provided on a bottom portion 11b located on the other end side (side opposite to the first cartridge 20) of the power supply unit case 11 in the longitudinal direction X. The charge terminal 43 is provided on a side surface of the bottom portion 11b, and at least one of a USB terminal, a micro USB terminal, or a Lightning (registered trademark) terminal can be connected thereto, for example.

The charge terminal 43 may be a power receiving unit capable of wirelessly receiving power transmitted from the external power supply. In such a case, the charge terminal 43 (power receiving unit) may be configured by a power receiving coil. The method of wirelessly transmitting power (wireless power transfer) may be an electromagnetic induction type or a magnetic resonance type. Moreover, the charge terminal 43 may also be a power receiving unit capable of receiving power transmitted from the external power supply in a non-contact manner. As another example, the charge terminal 43 is connectable with at least one of a USB terminal, a micro USB terminal, and a Lightning terminal, and may include the power receiving unit described above.

Figure 3:
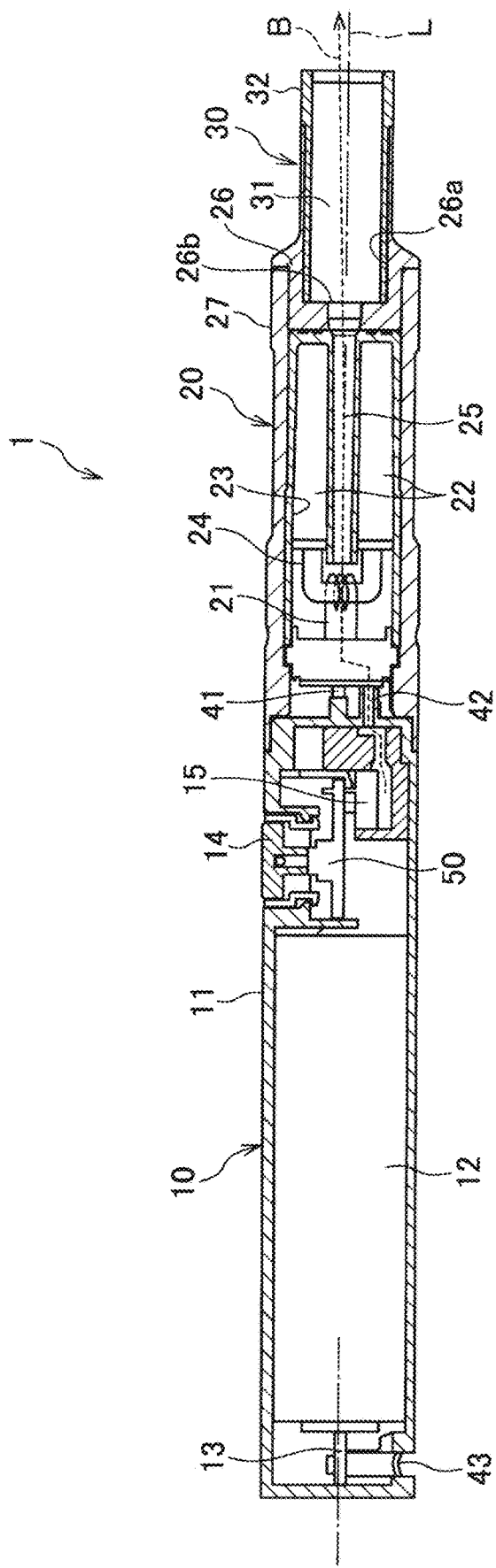
FIG. 3 is a cross-sectional view of the aerosol inhaler of FIG. 1.

An operation portion 14 that can be operated by a user is provided in the power supply unit case 11 so as to face a side opposite to the charge terminal 43 on a side surface of the top unit 11a. More specifically, the operation portion 14 and the charge terminal 43 have a point-symmetric relationship with respect to an intersection of a straight line connecting the operation portion 14 and the charge terminal 43 and a center line of the power supply unit 10 in the longitudinal direction X. The operation portion 14 is configured by a button type switch, a touch panel, or the like. As illustrated in FIG. 3, the intake sensor 15 configured to detect a puff operation is provided in the vicinity of the operation portion 14.

The charger 13 is arranged in proximity to the charge terminal 43, and controls charging of power input from the charge terminal 43 to the power supply 12. The charger 13 may also be arranged in the vicinity of the control circuit 50.

Figure 5:
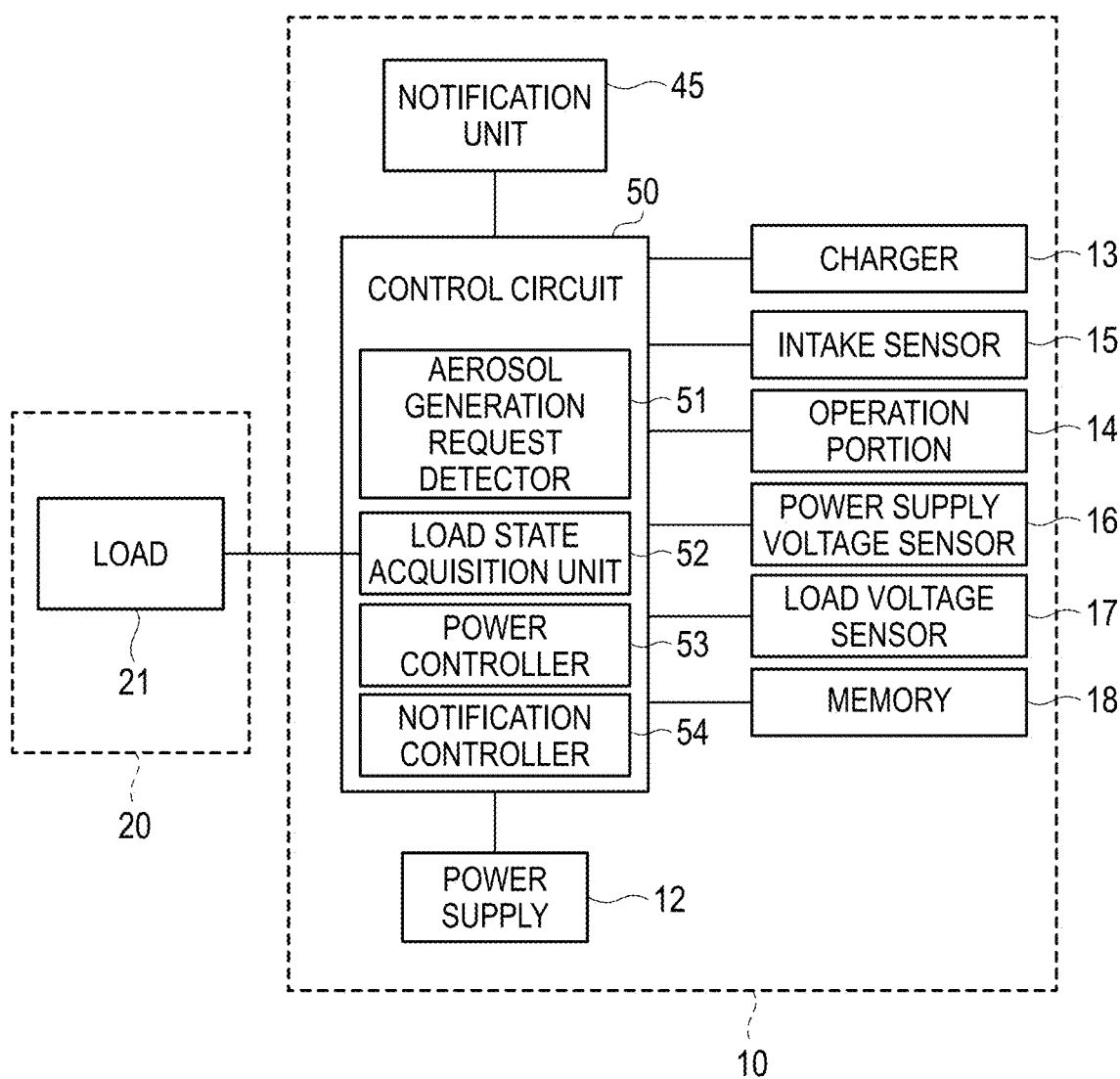
FIG. 5 is a block diagram illustrating a functional configuration of the aerosol inhaler of FIG. 1.

The control circuit 50 is, as illustrated in FIG. 5, connected to various sensor devices such as the intake sensor 15 configured to detect the puff (intake) operation, a power supply voltage sensor 16 configured to measure a voltage of the power supply 12, and a load voltage sensor 17 configured to measure a voltage applied to the load 21, the operation portion 14, a notification unit 45 to be described below, and a memory 18 configured to store the number of times of puff operations, a time of energization to the load 21 and the like. The control circuit 50 performs various controls of the aerosol inhaler 1. Specifically, the control circuit 50 mainly includes a processor 55 (see FIG. 8), which will be described below, and further includes storage media, such as a random access memory (RAM) necessary for the processor 55 to operate and a read only memory (ROM) configured to store various types of information. More specifically, the processor in the present specification is an electric circuit in which circuit elements such as semiconductor elements are combined.

The control circuit 50 may be configured such that the power supply voltage sensor 16 is provided inside the control circuit 50. In this case, the power supply voltage sensor 16 may be configured by an operational amplifier 56 and an analog-digital converter 57 to be described below. An output signal of the power supply voltage sensor 16 may be input to the processor 55 inside the control circuit 50.

The power supply unit case 11 is provided with an air intake opening (not illustrated) configured therein to take in outside air. The air intake opening may be provided around the operation portion 14, or may be provided around the charge terminal 43.

(First Cartridge)

As illustrated in FIG. 3, inside a cylindrical cartridge case 27, the first cartridge 20 includes: a reservoir 23 configured to store an aerosol source 22; the electric load 21 configured to atomize the aerosol source 22; a wick 24 configured to draw the aerosol source from the reservoir 23 to the load 21; an aerosol flow path 25 through which an aerosol generated by the atomization of the aerosol source 22 flows toward the second cartridge 30; and an end cap 26 configured to accommodate a part of the second cartridge 30.

The reservoir 23 is partitioned and formed so as to surround a periphery of the aerosol flow path 25, and stores the aerosol source 22. A porous body, such as a resin web or cotton, may be accommodated in the reservoir 23, and the aerosol source 22 may be impregnated in the porous body. The reservoir 23 may only store the aerosol source 22 without accommodating the resin web or the cotton porous body. The aerosol source 22 includes a liquid, such as glycerin, propylene glycol, or water.

The wick 24 is a liquid holding member configured to draw the aerosol source 22 from the reservoir 23 to the load 21 by utilizing a capillary phenomenon. The wick 24 is made of, for example, glass fiber or porous ceramic.

The load 21 performs atomization by heating the aerosol source 22 by power supplied from the power supply 12 via the discharge terminal 41 without burning. The load 21 is formed of an electric heating wire (coil) wound at a predetermined pitch.

The load 21 may be any element that can perform atomization by heating the aerosol source 22 to generate the aerosol. The load 21 is, for example, a heating element. Examples of the heating element include a heating resistor, a ceramic heater, and an induction heating type heater. Hereinafter, an electric resistance value of the load 21 will be referred to as an electric resistance value $R_H$.

A load whose temperature and electric resistance value are correlated is used as the load 21. More specifically, a load having a positive temperature coefficient (PTC) characteristic, which causes the electric resistance value to increase as the temperature increases, is used as the load 21. An example of the load 21 having the PTC characteristic is NiCr (nichrome). The load 21 having the PTC characteristic can also be realized by stainless steel, tungsten, or the like. The PTC characteristic is also referred to as a positive resistance temperature coefficient characteristic.

A coefficient indicating magnitude of an amount of change in the electric resistance value of the load 21 with respect to an amount of change in the temperature of the load 21 is referred to as a resistance temperature coefficient α [ppm (parts per million)/° C.]. The resistance temperature coefficient α can be expressed by the following formula (F1), where T refers to the temperature of the load 21, $T_{REF}$ refers to a reference temperature, and $R_{REF}$ refers to a reference electric resistance value.

[Formula 1]

$$\alpha\ [\text{ppm/° C.}] = \frac{R_H - R_{REF}}{R_{REF}} \cdot \frac{1}{T - T_{REF}} \cdot 10^6 \quad \text{(F1)}$$

For example, information indicating the resistance temperature coefficient CX [ppm/° C.] of the load 21 is stored in advance in the power supply unit 10 (for example, the memory 18 to be described below).

The aerosol flow path 25 is downstream of the load 21 and is provided on a center line L of the power supply unit 10. The end cap 26 includes: a cartridge accommodating portion **26*a* configured to accommodate a part of the second cartridge 30; and a communication path 26*b* configured to communicate the aerosol flow path 25 and the cartridge accommodating portion 26*a***.

(Second Cartridge)

The second cartridge 30 stores a flavor source 31. The second cartridge 30 is detachably accommodated in the cartridge accommodating portion **26*a* provided in the end cap 26 of the first cartridge 20. An end portion, which is located on a side opposite to the side of the first cartridge 20, of the second cartridge 30 serves as a user inhale opening 32. The inhale opening 32 is not limited to be formed integrally with the second cartridge 30, and may also be detachable from the second cartridge 30. By forming the inhale opening 32 separately from the power supply unit 10 and the first cartridge 20 in this way, the inhale opening 32** can be kept hygienic.

The second cartridge 30 passes the aerosol generated by atomizing the aerosol source 22 by the load 21 through the flavor source 31 and thus imparts a flavor to the aerosol. Chopped tobacco or a molded body obtained by molding a tobacco raw material into particles can be used as a raw material piece that forms the flavor source 31. The flavor source 31 may also be formed of a plant other than tobacco (for example, mint, Chinese herb, or herb). The flavor source 31 may be provided with a fragrance such as menthol.

In the aerosol inhaler 1 of the present embodiment, the flavored aerosol can be generated by the aerosol source 22, the flavor source 31, and the load 21. That is, the aerosol source 22 and the flavor source 31 constitute an aerosol generation source that generates the aerosol.

The aerosol generation source of the aerosol inhaler 1 is a portion that is replaced and used by the user. As this portion, for example, one first cartridge 20 and one or a plurality of (for example, five) second cartridges 30 are provided to the user as a set.

In addition to a configuration in which the aerosol source 22 and the flavor source 31 are separated from each other, a configuration in which the aerosol source 22 and the flavor source 31 are integrally formed, a configuration in which the flavor source 31 is omitted and substances that may be included in the flavor source 31 are added to the aerosol source 22, or a configuration in which a medicine or the like is added to the aerosol source 22 instead of the flavor source 31 may also be employed as the configuration of the aerosol generation source used in the aerosol inhaler 1.

In a case where the aerosol inhaler 1 includes the aerosol generation source in which the aerosol source 22 and the flavor source 31 are integrally formed, for example, one or a plurality of (for example, 20) aerosol generation sources are provided as a set to the user.

In a case where the aerosol inhaler 1 only includes the aerosol source 22 as the aerosol generation source, for example, one or a plurality of (for example, 20) aerosol generation sources are provided as a set to the user.

In the aerosol inhaler 1 configured in this way, as indicated by arrow B in FIG. 3, air flowing in from the intake opening (not illustrated) provided in the power supply unit case 11 passes through the vicinity of the load 21 of the first cartridge 20 from the air supply unit 42. The load 21 atomizes the aerosol source 22 drawn from the reservoir 23 by the wick 24. The aerosol generated by the atomization flows through the aerosol flow path 25 together with the air flowing in from the intake opening, and is supplied to the second cartridge 30 via the communication path **26*b*. The aerosol supplied to the second cartridge 30 passes through the flavor source 31 so as to be flavored, and is then supplied to the inhale opening 32**.

The aerosol inhaler 1 is provided with the notification unit 45 configured to notify various types of information (see FIG. 5). The notification unit 45 may be configured by a light emitting element, a vibrating element, or a sound output element. The notification unit 45 may also be a combination of two or more elements among the light emitting element, the vibrating element, and the sound output element. The notification unit 45 may be provided in any one of the power supply unit 10, the first cartridge 20, and the second cartridge 30, and is preferably provided in the power supply unit 10. For example, a configuration in which a periphery of the operation portion 14 has a light-transmitting property and light is emitted by a light emitting element such as an LED is employed.

(Electric Circuit of Power Supply Unit)

Next, a main part of an electric circuit of the power supply unit 10 will be described with reference to FIG. 6.

Figure 6:
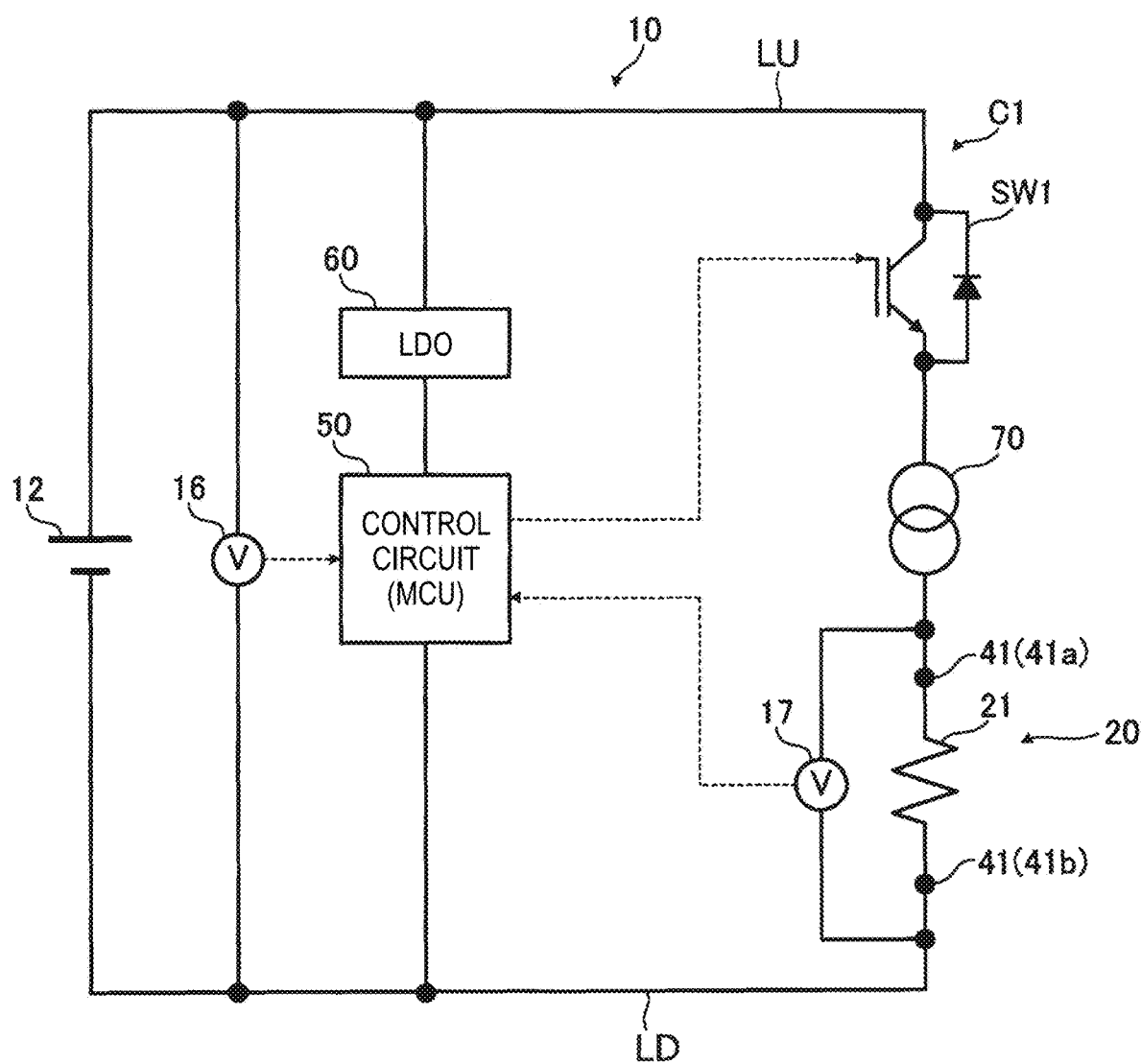
FIG. 6 illustrates a main circuit configuration of the power supply unit.

As illustrated in FIG. 6, the power supply unit 10 includes: the power supply 12; the power supply voltage sensor 16; the control circuit 50; a low drop out (LDO) regulator 60; the discharge terminal 41 connected to the load 21; a first switch SW1; a constant current circuit 70; and the load voltage sensor 17. The first switch SW1, the constant current circuit 70, the discharge terminal 41 connected to the load 21 and the load voltage sensor 17 constitute a heating and measurement circuit C1 to be described below.

In the power supply unit 10, the control circuit 50 is connected in series with the LDO regulator 60. The control circuit 50 and the LDO regulator 60 which are connected in series are connected to a main positive bus LU which is connected to a positive terminal of the power supply 12 and a main negative bus LD which is connected to a negative terminal of the power supply 12. Specifically, the control circuit 50 and the LDO regulator 60 are connected to the main positive bus LU and the main negative bus LD in a state where the LDO regulator 60 is on the side of the main positive bus LU while the control circuit 50 is on the side of the main negative bus LD.

The LDO regulator 60 is a voltage converter that converts a voltage applied by the power supply 12 (hereinafter also referred to as a "power supply voltage" of 4.2 [V], for example) into a predetermined voltage (a reference voltage $V_{REF}$ of 3.7 [V], for example). The LDO regulator 60 outputs the converted voltage to the control circuit 50.

The power supply voltage sensor 16 is connected in parallel to the power supply 12, and the control circuit 50 and the LDO regulator 60 which are connected in series, and has one end connected to the main positive bus LU while the other end connected to the main negative bus LD. As a result, the power supply voltage sensor 16 can detect a voltage between the main positive bus LU and the main negative bus LD. Moreover, the power supply voltage sensor 16 is also connected to the control circuit 50, and sends information indicating the detected voltage to the control circuit 50. As a result, the power supply voltage sensor 16 can notify the control circuit 50 of the detected voltage. Hereinafter, the voltage detected by the power supply voltage sensor 16 is also referred to as a "power supply voltage".

In FIG. 6, the heating and measurement circuit C1 is configured such that the first switch SW1, the constant current circuit 70, and the discharge terminal 41 connected to the load 21 are directly connected in such an order. An end portion, which is located on the side of the first switch SW1, of the heating and measurement circuit C1 is connected to the main positive bus LU. An end portion, which is located on the side of the discharge terminal 41, of the heating and measurement circuit C1 is connected to the main negative bus LD.

The first switch SW1 is a switch which is connected to the control circuit 50 and is opened and closed under control of the control circuit 50. The first switch SW1 is, for example, a MOSFET. In this case, the control circuit 50 can control the opening and closing of the first switch SW1 and a value of a current flowing through the first switch SW1 by controlling a gate voltage of the first switch SW1. An arrangement position of the first switch SW1 in the heating and measurement circuit C1 is not limited to a position between the main positive bus LU and the constant current circuit 70. As another example, the first switch SW1 may be arranged between the constant current circuit 70 and the load 21 or between the load 21 and the main negative bus LD.

The constant current circuit 70 outputs a constant current to the discharge terminal 41 (that is, the load 21) when a current is input. Specifically, the constant current output by the constant current circuit 70 has a predetermined current value that is equal to or less than that of the input current. By providing such a constant current circuit 70, the current input to the load 21 can be made constant without requiring a circuit that tends to be expensive and large in circuit scale, such as a DC/DC converter. Information indicating the current value of the constant current output by the constant current circuit 70 is stored in advance in the control circuit 50. Hereinafter, the current value of the constant current output by the constant current circuit 70 is also referred to as a "constant current value".

The load voltage sensor 17 is connected in parallel with the load 21 (that is, the discharge terminal 41) in the heating and measurement circuit C1 to detect a voltage applied to the load 21. Here, the voltage applied to the load 21 is an inter-terminal voltage between a positive electrode side discharge terminal 41a of the discharge terminal 41 and a negative electrode side discharge terminal 41b of the discharge terminal 41. Hereinafter, the voltage applied to the load 21 is also referred to as a "load voltage". Moreover, the load voltage sensor 17 is also connected to the control circuit 50, and sends load voltage information indicating the detected load voltage to the control circuit 50. As a result, the load voltage sensor 17 can notify the control circuit 50 of the detected load voltage.

According to the power supply unit 10 illustrated in FIG. 6, in a case where the load 21 is connected to the discharge terminal 41, when the control circuit 50 turns on the first switch SW1, a current from the power supply 12 is input to the constant current circuit 70, and the constant current circuit 70 outputs the constant current to the load 21. Therefore, in this case, the control circuit 50 can acquire the electric resistance value $R_H$ and a temperature T of the load 21 based on the detected load voltage and the constant current value, as will be described below.

(One Example of Circuit Configuration of Constant Current Circuit)

Next, an example of a circuit configuration of the constant current circuit 70 will be described with reference to FIG. 7.

Figure 7:
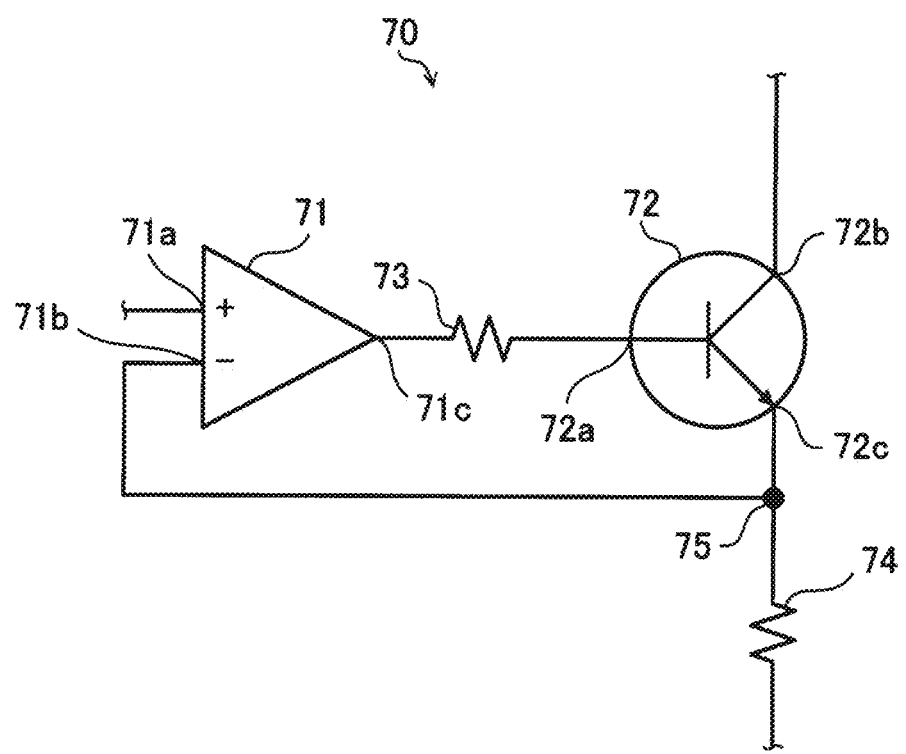
FIG. 7 illustrates an example of a constant current circuit.

As illustrated in FIG. 7, the constant current circuit 70 includes: an operational amplifier 71; a transistor 72; a resistor 73 and a resistor 74 which have predetermined electric resistance values.

The operational amplifier 71 includes: a non-inverting input terminal (+) 71a; an inverting input terminal (−) 71b; an output terminal 71c; and a pair of power supply terminals (not illustrated). The operational amplifier 71 amplifies a difference value obtained by subtracting a voltage input to the inverting input terminal 71b from a voltage input to the non-inverting input terminal 71a by a predetermined amplification factor, and outputs the amplified voltage from the output terminal 71c. Here, it is assumed that the amplification factor of the operational amplifier 71, that is, a net voltage gain of the operational amplifier 71 is sufficiently large.

The transistor 72 is an NPN transistor including: a base 72a; a collector 72b; and an emitter 72c. That is, in the transistor 72, a base current flowing in the base 72a and a collector current flowing in the collector 72b flow to the emitter 72c.

The base 72a is connected to the output terminal 71c of the operational amplifier 71 via the resistor 73. It should be noted that the resistor 73 may also be omitted. The collector 72b is connected to, for example, the first switch SW1 illustrated in FIG. 6. That is, the collector current is, for example, a current input to the constant current circuit 70 when the first switch SW1 is turned on. The emitter 72c is connected to, for example, the positive electrode side discharge terminal 41a illustrated in FIG. 6 via the resistor 74. A branch portion 75 is provided between the emitter 72c and the resistor 74. The branch portion 75 is connected to the inverting input terminal 71b of the operational amplifier 71. A predetermined voltage higher than a voltage that can be applied to the inverting input terminal 71b is input to the non-inverting input terminal 71a of the operational amplifier 71.

Since output of the operational amplifier 71 increases as the collector current decreases, the constant current circuit 70 increases the base voltage such that more collector current is flowed. In this way, the base voltage is adjusted until the voltages input to the non-inverting input terminal 71a and the inverting input terminal 71b are approximately equal to each other. As a result, the collector current is approximately equal to a value obtained by dividing a value of the voltage input to the non-inverting input terminal 71a by the electric resistance value of the resistor 74. Since the value of the voltage input to the non-inverting input terminal 71a and the electric resistance value of the resistor 74 are constants, the collector current is also controlled to be a constant value.

According to the constant current circuit 70 illustrated in FIG. 7, the constant current can be output from the emitter 72c in response to an inflow of the collector current to the collector 72b. By using such a constant current circuit 70, the current input to the load 21 can be made constant with a simple configuration which does not require a circuit that tends to be expensive and large in circuit scale, such as a DC/DC converter. The constant current circuit 70 illustrated in FIG. 7 is an example, and is not intended to limit the configuration of the constant current circuit 70. For example, the constant current circuit 70 may also be realized by using a known circuit, such as a current mirror circuit.

(Configuration of Control Device)

Next, a configuration of the control circuit 50 will be described in more detail.

As illustrated in FIG. 5, the control circuit 50 includes an aerosol generation request detector 51, a load state acquisition unit 52, a power controller 53, and a notification controller 54 as functional blocks realized by a processor executing a program stored in a ROM.

The aerosol generation request detector 51 detects an aerosol generation request based on an output result of the intake sensor 15. The intake sensor 15 is configured to output a value of a pressure (internal pressure) change in the power supply unit 10 caused by inhale of the user through the inhale opening 32. The intake sensor 15 is, for example, a pressure sensor that outputs an output value (for example, a voltage value or a current value) corresponding to an internal pressure that changes in accordance with a flow rate of air inhaled from the intake opening (not illustrated) toward the inhale opening 32 (that is, the puff operation of the user). The intake sensor 15 may be configured by a condenser microphone or the like. The intake sensor 15 may output an analog value, or may output a digital value converted from the analog value.

The load state acquisition unit 52 acquires the electric resistance value or the temperature of the load 21 based on an electric variable and a predetermined constant of the load 21. The electric variable of the load 21 can be, for example, the load voltage detected by the load voltage sensor 17. The predetermined constant can be, for example, the current value of the constant current output by the constant current circuit 70 to the load 21 (constant current value).

Here, the load voltage detected by the load voltage sensor 17 is referred to as $V_H$, the constant current value output by the constant current circuit 70 is referred to as $I_H$, the electric resistance value of the load 21 is referred to as $R_H$, and the temperature of the load 21 is referred to as T. In this case, the electric resistance value $R_H$ of the load 21 can be expressed by the following formula (F2).

[Formula 2]

$$R_H = V_H / I_H \quad (F2)$$

Here, the load voltage $V_H$ is a value that can be acquired from the load voltage sensor 17, and the constant current value $I_H$ is a value stored in advance in the memory 18 or the like. Therefore, the load state acquisition unit 52 can obtain the electric resistance value $R_H$ of the load 21 by substituting the load voltage $V_H$ and the constant current value $I_H$ into the above formula (F2). As represented in the above formula (F1), the electric resistance value $R_H$ and the temperature T of the load 21 are correlated. Therefore, the load state acquisition unit 52 can acquire the temperature T of the load 21 from the acquired electric resistance value $R_H$ of the load 21 and the above formula (F1).

The notification controller 54 controls the notification unit 45 to notify various types of information. For example, the notification controller 54 controls the notification unit 45 to notify replacement timing of the second cartridge 30 in response to detection of the replacement timing of the second cartridge 30. The notification controller 54 detects and notifies the replacement timing of the second cartridge 30 based on the cumulative number of times of puff operations or a cumulative energization time to the load 21 stored in the memory 18. The notification controller 54 is not limited to only notify the replacement timing of the second cartridge 30, and may also notify replacement timing of the first cartridge 20, replacement timing of the power supply 12, charging timing of the power supply 12 and the like.

The notification controller 54 determines that the second cartridge 30 has been used up (for example, a remaining amount is zero or empty), and notifies the replacement timing of the second cartridge 30 in a case where one unused second cartridge 30 is set and then the puff operation is performed a predetermined number of times or in a case where the cumulative energization time to the load 21 reaches a predetermined value (for example, 120 seconds) due to the puff operation.

The notification controller 54 may determine that one first cartridge 20 included in one set has been used up (for example, the remaining amount is zero or empty), and notifies the replacement timing of the first cartridge 20 in a case where it is determined that all the second cartridges 30 included in the above one set have been used up.

When the aerosol generation request detector 51 detects the aerosol generation request, the power controller 53 controls discharge of the power supply 12 via the discharge terminal 41 by, for example, on/off of the first switch SW1.

The power controller 53 performs control such that an amount of aerosol generated by atomizing the aerosol source by the load 21 falls within a desired range, in other words, an amount of power supplied from the power supply 12 to the load 21 falls within a certain range. Specifically, the power controller 53 controls the on/off of the first switch SW1 by, for example, pulse width modulation (PWM) control. Instead of the PWM control, the power controller 53 may also control the on/off of the first switch SW1 by pulse frequency modulation (PFM) control.

The power controller 53 may stop power supply from the power supply 12 to the load 21 when a predetermined period of time has elapsed since the power supply to the load 21 was started. In other words, the power controller 53 stops the power supply from the power supply 12 to the load 21 when a puff period exceeds a predetermined period even within the puff period when the user actually performs the puff operation. The predetermined period is set in order to reduce variations in the puff period of the user. The power controller 53 controls a duty ratio of on/off of the switch 19 during one puff operation in accordance with an amount of electricity stored in the power supply 12. For example, the power controller 53 controls an on-time interval (pulse interval) for supplying power from the power supply 12 to the load 21, and controls an on-time length (pulse width) for supplying power from the power supply 12 to the load 21.

The power controller 53 detects electric connection between the charge terminal 43 and the external power supply 60, and controls charging of the power supply 12 via the charger 13.

(Temperature Resolution of Load Detectable by Control Device)

Next, resolution of the temperature T of the load 21 that can be detected (acquired) by the control circuit 50 will be considered. Hereinafter, the resolution of the temperature T of the load 21 that can be detected by the control circuit 50 is also referred to as "temperature resolution".

(Specific Configuration for Acquiring Load Temperature and the Like)

Figure 8:
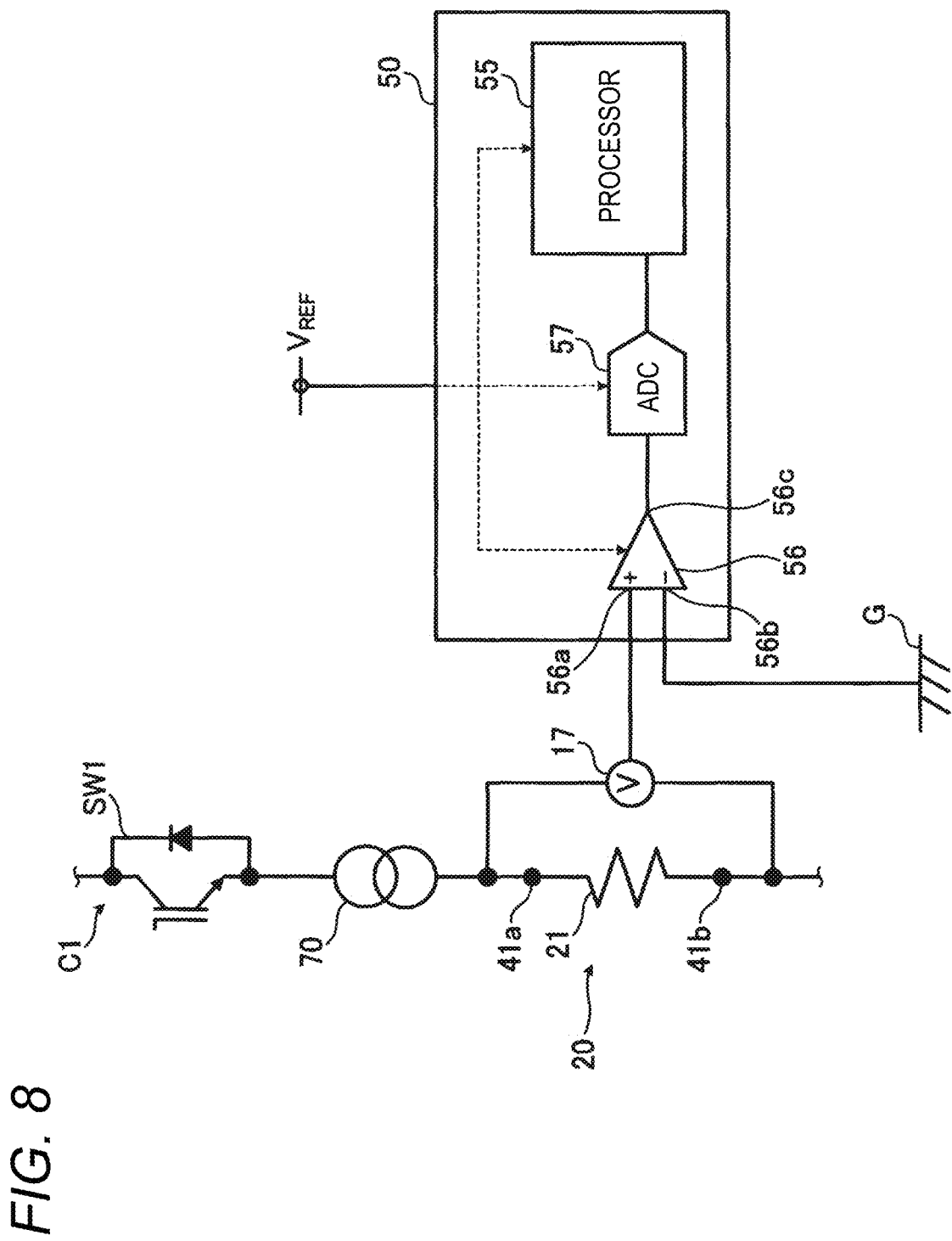
FIG. 8 is a main part enlarged view of a circuit configuration of the power supply unit of FIG. 6.

FIG. 8 is a main part enlarged view of a circuit configuration of the power supply unit 10 illustrated in FIG. 6. As illustrated in FIG. 8, the control circuit 50 includes: the operational amplifier 56; the analog-digital converter (ADC) 57; and the processor 55. The operational amplifier 56 and the analog-digital converter 57 may also be provided outside the control circuit 50.

The operational amplifier 56 includes: a non-inverting input terminal (+) 56a; an inverting input terminal (−) 56b; an output terminal 56c; and a pair of power supply terminals. The operational amplifier 56 amplifies a difference value obtained by subtracting a voltage input to the inverting input terminal 56b from a voltage input to the non-inverting input terminal 56a by a predetermined amplification factor (hereinafter referred to as "amplification factor A"), and outputs the amplified voltage from the output terminal 56c to the analog-digital converter 57.

Specifically, the non-inverting input terminal 56a of the operational amplifier 56 is connected to the load voltage sensor 17. As a result, a voltage signal (analog signal) indicating output of the load voltage sensor 17, that is, the load voltage $V_H$, is applied to the non-inverting input terminal 56a as an input voltage $V_{IN}$. The input voltage $V_{IN}$ varies in accordance with a change in the electric resistance value $R_H$ of the load 21. Therefore, an amount of change in the input voltage $V_{IN}$ with respect to an amount of change in the electric resistance value $R_H$ of the load 21 is hereinafter referred to as $\Delta V_{IN}$.

The inverting input terminal 56b of the operational amplifier 56 is connected to, for example, ground G, and the voltage input to the inverting input terminal 56b is "0 (zero)". Therefore, a voltage signal $A \cdot V_{IN}$ (analog signal) obtained by amplifying the input voltage $V_{IN}$ by the amplification factor A is output from the output terminal 56c of the operational amplifier 56, and is input to the analog-digital converter 57. Moreover, the pair of power supply terminals of the operational amplifier 56 includes a high potential side power supply terminal and a low potential side power supply terminal. The reference voltage Vu is input to the high potential side power supply terminal, for example. The low potential side power supply terminal is connected to, for example, the ground G. As illustrated in FIG. 8, the reference voltage $V_{REF}$ is also input to the processor 55 as a power supply voltage of the processor 55, for example.

Here, the amplification factor A of the operational amplifier 56 is set to 1. In other words, the operational amplifier 56 does not perform amplification. In this way, by setting the amplification factor A of the operational amplifier 56 to be 1, noise amplification caused by the operational amplifier 56 can be prevented, and it is possible to accurately detect the electric resistance value $R_H$ and the temperature T of the load 21. It should be noted that output from the load voltage sensor 17 may be directly input to the analog-digital converter 57 without providing the operational amplifier 56, and the same effect as when the amplification factor A is set to 1 can be obtained even with such a configuration.

The analog-digital converter 57 operates through using the reference voltage $V_{REF}$ output from the LDO regulator 60 as a power supply, converts the voltage signal $A \cdot V_N$ input from the operational amplifier 56 into a digital signal, and outputs the converted digital signal to the processor 55. An analog-digital converter which has an N-bit resolution that operates according to the reference voltage $V_{REF}$ is used as the analog-digital converter 57.

Here, a resolution Res [V/bit] of the N-bit analog-digital converter 57 to which the reference voltage $V_{REF}$ is input as the power supply can be expressed by the following formula (F3).

[Formula 3]

$$Res\ [V/bit] = \frac{V_{REF}}{2^N} \tag{F3}$$

When the above formula (F3) is rewritten such that a dimension of the resolution Res changes from [V/bit] to [° C.], the temperature resolution Res [° C.] of the control circuit 50 with respect to the temperature T of the load 21 can be expressed by the following formula (F4). $\Delta T_H (\Delta R_H)$ in the following formula (F4) represents an amount of change in the temperature T of the load 21 in accordance with an amount of change in the electric resistance value $R_H$ of the load 21. Therefore, by using the resistance temperature coefficient α [%] of the load 21, the following formula (F4) can be transformed into the following formula (F5).

[Formula 4]

$$Res\ [° C.] = \frac{\Delta T_H(\Delta R_H) \cdot Res\ [V/bit]}{\Delta V_{IN}} \tag{F4}$$

[Formula 5]

$$\begin{aligned}Res\ [° C.] &= \frac{1}{\alpha[\%]} \cdot \frac{1}{\Delta V_{IN}} \cdot Res\ [V/bit] \\ &= \frac{1}{\alpha[ppm/° C.] \times 10^2 \times 10^{-6}} \cdot \frac{1}{\Delta V_{IN}} \cdot Res\ [V/bit] \\ &= \frac{1}{\alpha[ppm/° C.] \times 10^{-4}} \cdot \frac{1}{\Delta V_{IN}} \cdot \frac{V_{REF}}{2^N}\end{aligned} \tag{F5}$$

As described above, here, the constant current value $I_H$ is input to the load 21 by the constant current circuit 70, and the amplification factor A of the operational amplifier 56 is set to 1. Therefore, the above formula (F5) can be transformed into the following formula (F6).

[Formula 6]

$$Res\ [^\circ C.] = \frac{1}{\alpha[\text{ppm}/^\circ C.] \times 10^{-4}} \cdot \frac{1}{\Delta V_{IN}} \cdot \frac{V_{REF}}{2^N} \quad (F6)$$
$$= \frac{1}{\alpha[\text{ppm}/^\circ C.] \times 10^{-4}} \cdot \frac{1}{I_H \cdot \Delta R_H} \cdot \frac{V_{REF}}{2^N}$$

As can be seen from the above formula (F6), in order to increase the temperature resolution Res [° C.], the constant current value $I_H$ output by the constant current circuit 70 may be increased.

In Formulas (F3) to (F6), the temperature resolution Res [° C.] of the load 21 has been described.

As described above, since the temperature and the electric resistance value of the load 21 are correlated, it can be understood that a resolution of the electric resistance value of the load 21 is also increased by increasing the constant current value $I_H$. In the following description, the temperature and the electric resistance value of the load 21 are treated as equivalent.

Figure 9:
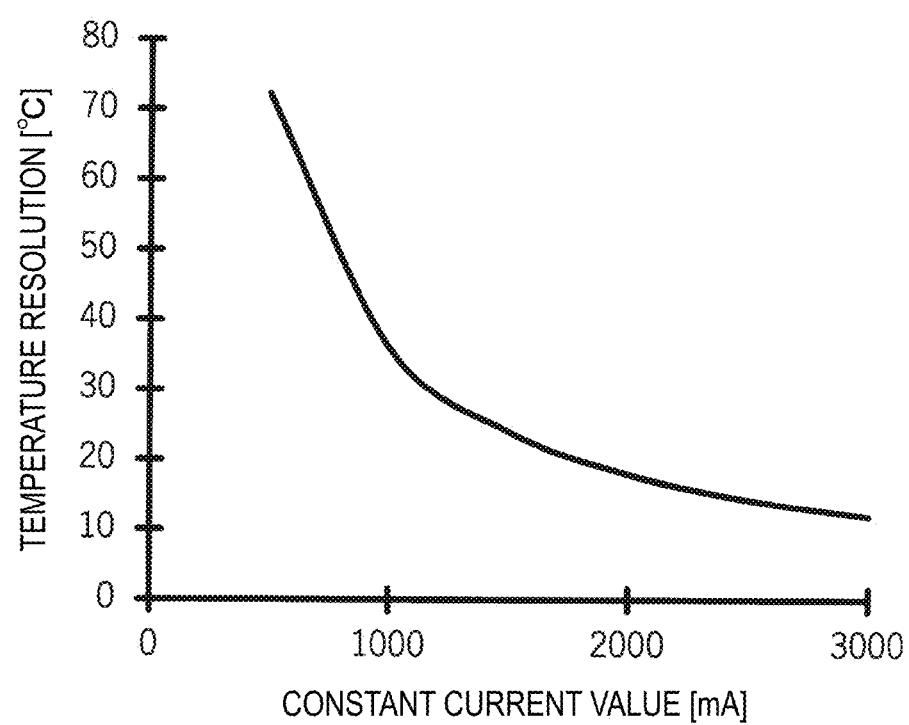
FIG. 9 illustrates an example of a relationship between a constant current output by the constant current circuit and a temperature resolution.

FIG. 9 illustrates an example of a relationship between the constant current value $I_H$ [mA] output by the constant current circuit 70 and the temperature resolution Res [° C.]. In FIG. 9, a horizontal axis indicates the constant current value $I_H$ [mA], and a vertical axis indicates the temperature resolution Res [° C.]. In the example of FIG. 9, the resistance temperature coefficient α of the load 21 is 100 [ppm/° C.], the amount of change $\Delta R_H$ of the electric resistance value $R_H$ of the load 21 is 1 [%], the reference voltage $V_{REF}$ is 3.7 [V], and N is 10 [bit].

As illustrated in FIG. 9, by setting the constant current value $I_H$ output by the constant current circuit 70 to about 1000 [mA] (that is, 1 [A]), the temperature resolution Res [° C.] can be set to about 30 to 40 [° C.]. Therefore, by setting the constant current value $I_H$ to 1 [A] or more, it is possible to detect the temperature T of the load 21 with accuracy required for detecting detachment and attachment of the first cartridge 20, for example. When the first cartridge 20 is not connected to the discharge terminal 41, a temperature (that is, the electric resistance value) acquired by the processor 55 greatly varies. Accordingly, if the temperature resolution Res [° C.] is about 30 to 40 [° C.], the detachment and attachment detection of the first cartridge 20 can be performed with sufficient accuracy.

As illustrated in FIG. 9, by setting the constant current value $I_H$ output by the constant current circuit 70 to about 2000 [mA] (that is, 2 [A]), the temperature resolution Res [° C.] can be set to about 20 to 30 [° C.]. Therefore, by setting the constant current value $I_H$ to 2 [A] or more, it is possible to detect the temperature T of the load 21 with higher accuracy. As a result, for example, it is possible to detect the temperature T of the load 21 with accuracy required to realize functions, such as identification of the first cartridge 20, authentication of an authentic product, or detection of remaining amount of the aerosol source (for example, depletion detection). That is, in these functions, the temperature (that is, the electric resistance value) acquired by the processor 55 is slightly different between states to be distinguished (for example, a state where the aerosol source remains and a state where the aerosol source is depleted in the case of detection of the remaining amount of the aerosol source). Accordingly, if the temperature resolution Res

[° C.] is about 20 to 30 [° C.], a certain degree of accuracy can be ensured and these functions can be realized.

As illustrated in FIG. 9, by setting the constant current value $I_H$ output by the constant current circuit 70 to about 3000 [mA] (that is, 3 [A]), the temperature resolution Res [° C.] can be set to about 10 to 20 [° C.]. Therefore, by setting the constant current value $I_H$ to 3 [A] or more, it is possible to detect the temperature T of the load 21 with still higher accuracy. As a result, through using the detected temperature T of the load 21, it is possible to realize the functions such as the identification of the first cartridge 20, the authentication of the authentic product or the detection of the remaining amount of the aerosol source (for example, the depletion detection) with higher accuracy. That is, if the temperature resolution Res [° C.] is about 10 to 20° C., such functions can be realized with sufficient accuracy.

(Control Process Performed by Control Device)

Next, a control process performed by the control circuit 50 to acquire the electric resistance value $R_H$ and the temperature T of the load 21 will be described.

Figure 10:
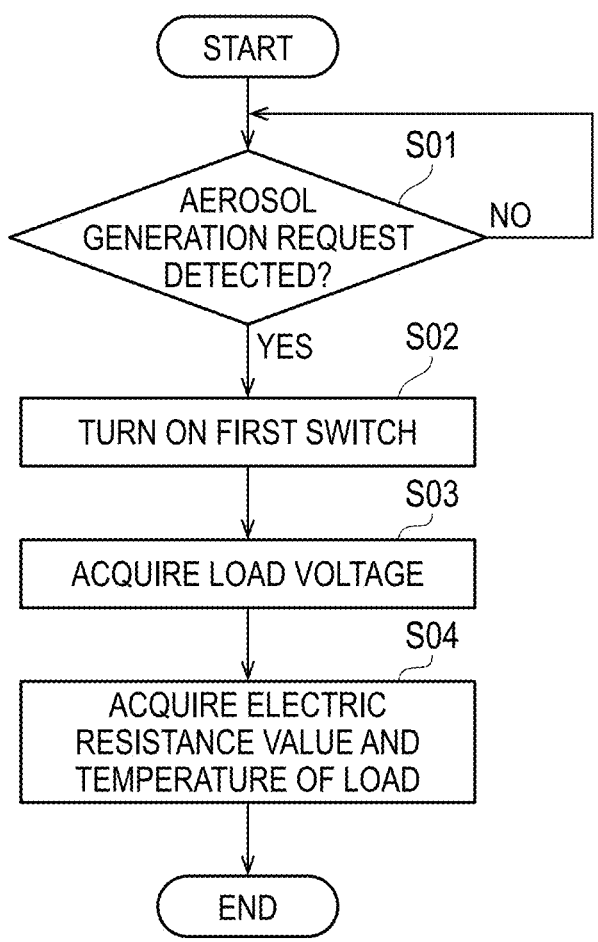
FIG. 10 is a flowchart illustrating a processing procedure of a control process performed by a control device of the power supply unit.

As illustrated in FIG. 10, the control circuit 50 first determines whether the aerosol generation request is detected based on the output result of the intake sensor 15 (step S01). When it is determined in step S01 that the aerosol generation request is detected (YES in step S01), the control circuit 50 turns on the first switch SW1 (step S02). As a result, the current from the power supply 12 is input to the constant current circuit 70, and the constant current circuit 70 outputs the constant current to the load 21.

Subsequently, the control circuit 50 acquires the load voltage $V_H$ detected by the load voltage sensor 17 (step S03). Then the control circuit 50 acquires the electric resistance value $R_H$ and the temperature T of the load 21 based on the load voltage $V_H$ acquired by step S03 and the constant current value $I_H$ output by the constant current circuit 70 to the load 21 (step S04), and ends the control process illustrated in FIG. 10.

As described above, the control circuit 50 can acquire the electric resistance value $R_H$ and the temperature T of the load 21 based on the load voltage $V_H$ detected by the load voltage sensor 17 and the constant current value $I_H$ output by the constant current circuit 70 to the load 21. Here, the constant current circuit 70 that outputs the constant current to the load 21 is realized by a simple configuration. Therefore, the control circuit 50 can acquire the electric resistance value $R_H$ and the temperature T of the load 21 with a simple configuration.

(First Modification of Aerosol Inhaler)

Next, a first modification of the aerosol inhaler 1 will be described. A main part of an electric circuit of the power supply unit 10 of the aerosol inhaler 1 of the first modification will be described with reference to FIG. 11. In the following description of FIG. 11, descriptions of the same portions as those in FIG. 6 will be omitted as appropriate.

Figure 11:
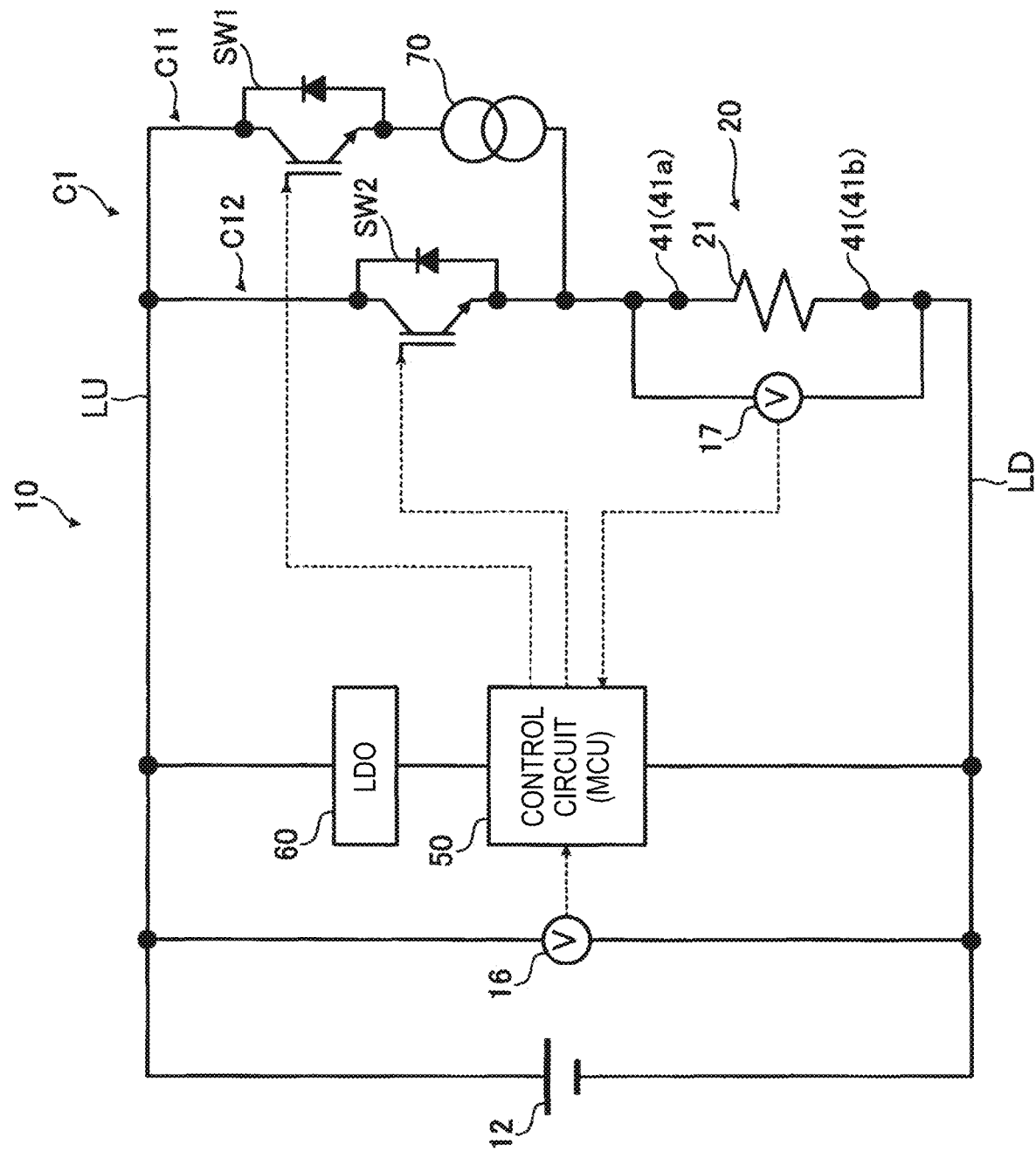
FIG. 11 illustrates a first modification of the power supply unit.

As illustrated in FIG. 11, in the power supply unit 10 of the first modification, a first circuit C11, which includes the first switch SW1 and the constant current circuit 70, and a second circuit C12, which includes a second switch SW2, are connected in parallel on an upstream side of the discharge terminal 41 (that is, the load 21) of the heating and measurement circuit C1, which is different from the example described in FIG. 6. Here, similarly to the first switch SW1, the second switch SW2 is connected to the control circuit 50 and opens and closes under the control of the control circuit 50.

In the first modification, for example, when the aerosol generation request is detected, the control circuit 50 turns on the second switch SW2 and turns off the first switch SW1. As a result, the current output from the power supply 12 is input to the load 21 by the second circuit C12. That is, in this case, a current that is not affected by the constant current circuit 70 can be input to the load 21. Therefore, a current whose current value is not reduced by the constant current circuit 70 can be input to the load 21, and the load 21 can be efficiently heated. In other words, a current without power loss caused by the constant current circuit 70 can be input to the load 21. As a result, inhale response of the aerosol and the like can be improved.

In the first modification, the control circuit 50 turns on the first switch SW1 and turns off the second switch SW2, for example, when an acquisition request of the electric resistance value $R_H$ and the temperature T of the load 21 is detected. As a result, the current output from the power supply 12 is input to the first circuit C11, and the constant current can be output to the load 21 by the constant current circuit 70. Therefore, in this case, the control circuit 50 can acquire the electric resistance value $R_H$ and the temperature T of the load 21 as in the above-described example.

(Second Modification of Aerosol Inhaler)

Next, a second modification of the aerosol inhaler 1 will be described. In the power supply unit 10 of the aerosol inhaler 1 of the second modification, the constant current value $I_H$ output by the constant current circuit 70 is small (for example, 100 [mA]), and therefore the amplification factor A of the operational amplifier 56 illustrated in FIG. 8 is set to be larger than 1.

When the amplification factor A of the operational amplifier 56 is not 1, the above formula (F5) can be transformed into the following formula (F7).

[Formula 7]
$$Res\ [°\ C.] = \frac{1}{\alpha[ppm/°\ C.] \times 10^{-4}} \cdot \frac{1}{A \cdot I_H \cdot \Delta R_H} \cdot \frac{V_{REF}}{2^N} \quad (F7)$$

It can be seen from the above formula (F7) that the temperature resolution Res [° C.] can be maintained or increased by increasing the amplification factor A of the operational amplifier 56 even if the constant current value $I_H$ output by the constant current circuit 70 is small.

Figure 12:
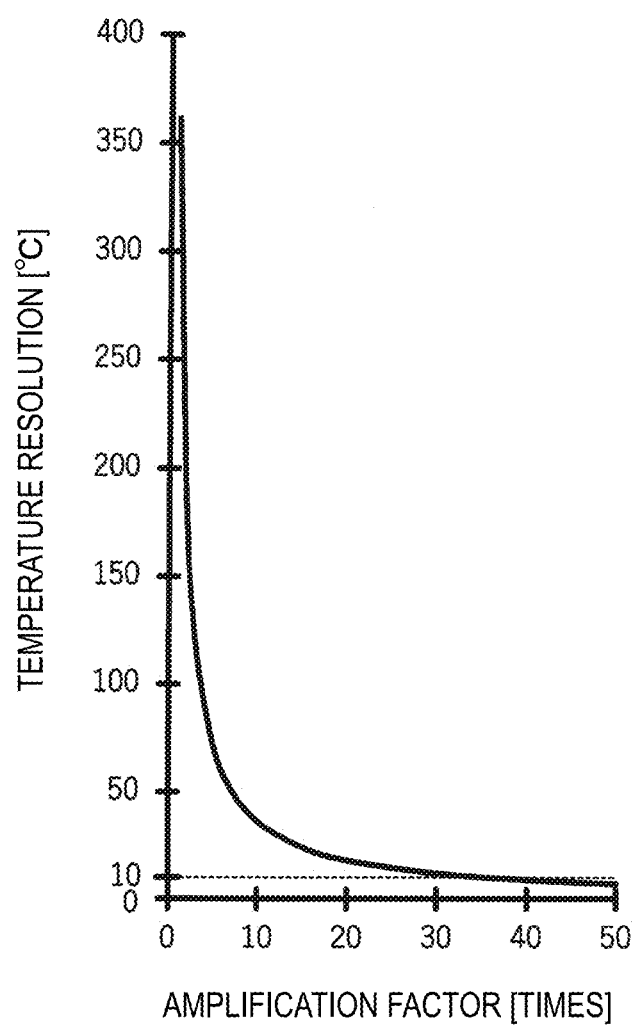
FIG. 12 illustrates an example of a relationship between an amplification factor of an operational amplifier included in the control device of the power supply unit and the temperature resolution.

FIG. 12 illustrates an example of a relationship between the amplification factor A of the operational amplifier 56 and the temperature resolution Res [° C.]. In FIG. 12, the horizontal axis indicates the amplification factor A [times], and the vertical axis indicates the temperature resolution Res [° C.]. In the example of FIG. 12, the constant current value $I_H$ output by the constant current circuit 70 is 100 [mA], the resistance temperature coefficient α of the load 21 is 100 [ppm/° C.], the amount of change $\Delta R_H$ of the electric resistance value $R_H$ of the load 21 is 1 [%], the reference voltage $V_{REF}$ is 3.7 [V], and N is 10 [bit].

As illustrated in FIG. 12, even if the constant current value $I_H$ output by the constant current circuit 70 is 100 [mA], the temperature resolution Res [° C.] similar to that of the example illustrated in FIG. 9 can be sufficiently ensured by increasing the amplification factor A of the operational amplifier 56. In particular, when the amplification factor A of the operational amplifier 56 is 40 times or more, the temperature resolution Res [° C.] can be set to 10 [° C.] or less even if the constant current value $I_H$ output by the constant current circuit 70 is reduced to about 100 [mA].

In this way, by setting the constant current value $I_H$ output by the constant current circuit 70 to less than 1 [A], preferably 100 [mA] or less, Joule heat generated in the load 21 can be reduced when the temperature T of the load 21 and the like are acquired. As a result, an influence of the Joule heat on the temperature T of the load 21 can be reduced, and the electric resistance value $R_H$ and the temperature T of the load 21 can be accurately detected.

It is also possible to combine the first modification and the second modification. That is, as illustrated in FIG. 11, the first circuit C11 which includes the first switch SW1 and the constant current circuit 70 and the second circuit C12 which includes the second switch SW2 are connected in parallel on the upstream side of the discharge terminal 41 (that is, the load 21) of the heating and measurement circuit C1, the constant current value $I_H$ output by the constant current circuit 70 is less than 1 [A] (for example, 100 [mA]), and therefore the amplification factor A of the operational amplifier 56 illustrated in FIG. 8 may be set to be greater than 1. More specifically, for example, the constant current value $I_H$ may be set to 100 [mA] and the amplification factor A may be set to 40 times.

(Third Modification of Aerosol Inhaler)

Next, a third modification of the aerosol inhaler 1 will be described. A main part of an electric circuit of the power supply unit 10 of the aerosol inhaler 1 of the third modification will be described with reference to FIG. 13. In the following description of FIG. 13, descriptions of the same portions as those in FIG. 11 will be omitted as appropriate.

Figure 13:
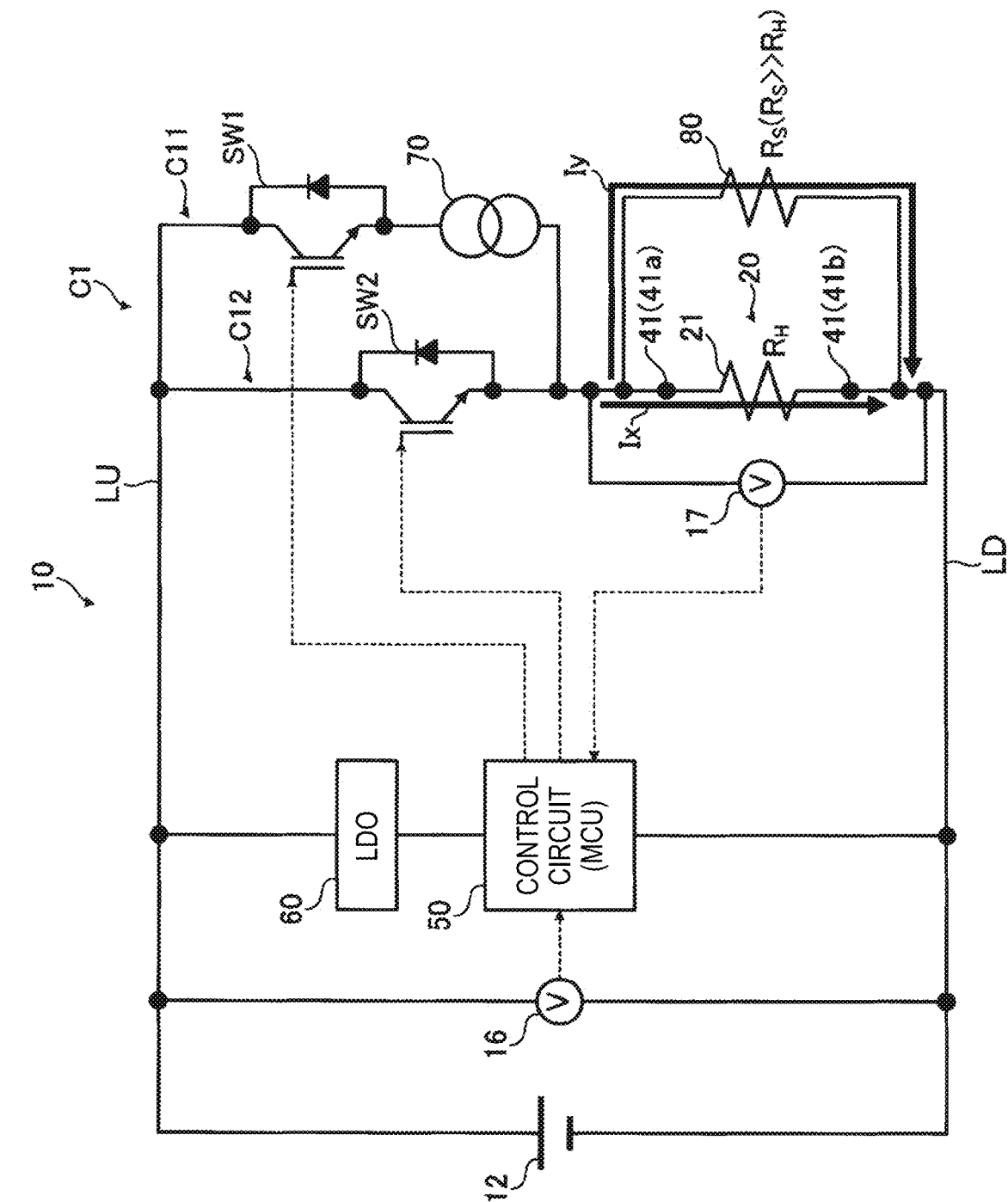
FIG. 13 illustrates a third modification of the power supply unit.

As illustrated in FIG. 13, in the power supply unit 10 of the third modification, a shunt resistor 80 which has a predetermined electric resistance value $R_S$ ($R_S \gg R_H$) is connected in parallel to the load 21 in the heating and measurement circuit C1, which is different from the example described in FIG. 11. As illustrated in FIG. 13, in the power supply unit 10 of the third modification, the load voltage sensor 17 is connected in parallel to the shunt resistor 80 and the load 21.

In a case where such a shunt resistor 80 is provided, when the first cartridge 20 is attached to the power supply unit 12 (that is, when the load 21 is connected to the discharge terminal 41), most of the constant current output by the constant current circuit 70 flows through the load 21, as indicated by arrow Ix of FIG. 13. Therefore, in this case, the load voltage $R_H$ is detected by the load voltage sensor 17.

On the other hand, when the first cartridge 20 is detached from the power supply unit 12, the constant current output by the constant current circuit 70 flows through the shunt resistor 80, as indicated by arrow Iy of FIG. 13. Therefore, in this case, the electric resistance value $R_S$ of the shunt resistor 80 is detected by the load voltage sensor 17. As described above, since the electric resistance value $R_S$ of the shunt resistor 80 is sufficiently larger than the electric resistance value $R_H$ of the load 21, the control circuit 50 can easily detect a state where the first cartridge 20 is detached from the power supply unit 12.

As described above, by providing the shunt resistor 80, the control circuit 50 can accurately detect attachment and detachment of the first cartridge 20 with respect to the power supply unit 12 based on a detection result of the load voltage sensor 17. Although detailed descriptions and drawings are omitted, in the power supply unit 12 illustrated in FIG. 6, the shunt resistor 80 may also be connected in parallel with the load 21 in the same manner as the power supply unit 12 illustrated in FIG. 13. In this case, it is also possible to accurately detect the attachment and detachment of the first cartridge 20 with respect to the power supply unit 12 based on the detection result of the load voltage sensor 17.

(Fourth Modification of Aerosol Inhaler)

Next, a fourth modification of the aerosol inhaler 1 will be described. A main part of an electric circuit of the power supply unit 10 of the aerosol inhaler 1 of the fourth modification will be described with reference to FIG. 14. In the following description of FIG. 14, descriptions of the same portions as those in FIG. 11 will be omitted as appropriate.

As described above, by increasing the constant current value $I_H$ output by the constant current circuit 70 to the load 21, the temperature resolution Res [° C.] can be increased. Since the constant current value $I_H$ is equal to or lower than the current value of the current input to the constant current circuit 70, it is necessary to increase the current value of the current input to the constant current circuit 70 so as to increase the constant current value $I_H$.

Figure 14:
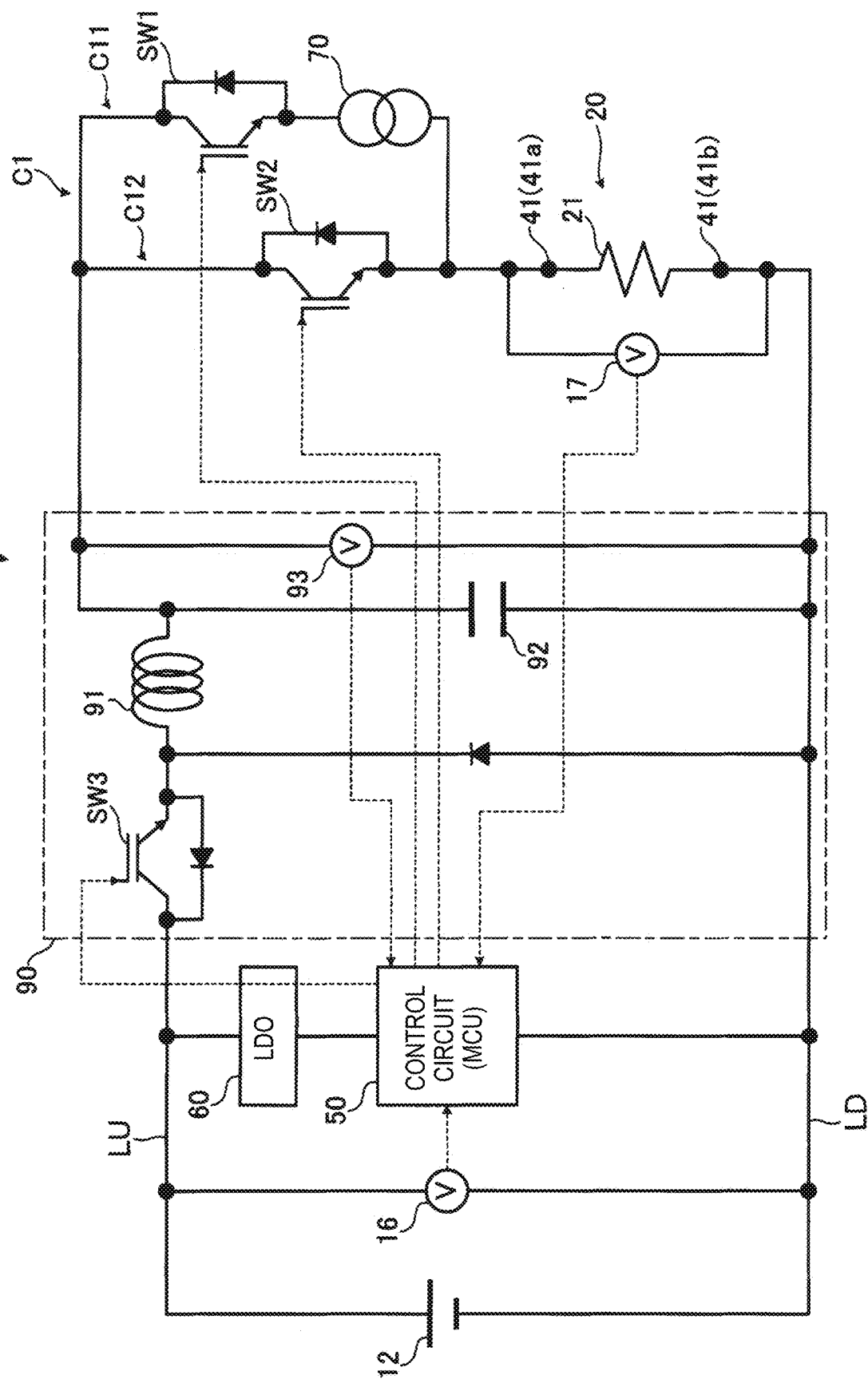
FIG. 14 is a first diagram illustrating a fourth modification of the power supply unit.

Therefore, in the power supply unit 10 of the fourth modification, as illustrated in FIG. 14, an amplifier circuit 90 is provided between the power supply 12 and the heating and measurement circuit C1, which is different from the example described in FIG. 11. The amplifier circuit 90 is a circuit that amplifies the current input from the power supply 12 and outputs the amplified current to the heating and measurement circuit C1. As a result, it is possible to input a current having a larger current value than a current that can be output from the power supply 12 to the constant current circuit 70.

Specifically, the amplifier circuit 90 includes a third switch SW3, a coil 91, a condenser 92, an amplifier circuit voltage sensor 93, and the like. The amplifier circuit 90 is a switching regulator (for example, a DC/DC regulator) capable of dropping an input voltage to a predetermined voltage, and amplifies an output current by dropping the input voltage.

Similarly to the first switch SW1 and the second switch SW2, the third switch SW3 is connected to the control circuit 50 and opens and closes under the control of the control circuit 50. The third switch SW3 is connected in series with the coil 91, and is connected to the main positive bus LU in a state where the third switch SW3 is on the side of the power supply 12 while the coil 91 is on the side of the heating and measurement circuit C1. An end portion, which is located on a side opposite to the side of the third switch SW3, of the coil 91 is connected to the condenser 92. An end portion, which is located on a side opposite to the side of the coil 91, of the condenser 92 is connected to the main negative bus LD. The amplifier circuit voltage sensor 93 is connected in parallel with the condenser 92 in the amplifier circuit 90, and detects a voltage output from the amplifier circuit 90 (hereinafter, also referred to as an "amplifier circuit output voltage"). The amplifier circuit voltage sensor 93 sends, for example, amplifier circuit output voltage information which indicates the detected amplifier circuit output voltage to the control circuit 50. It should be noted that the amplifier circuit 90 may also be controlled by a circuit different from the control circuit 50.

Here, it is assumed that the amplifier circuit 90 drops the input voltage to a voltage of 1/n (n is a predetermined value). Assuming that loss caused by voltage conversion (voltage drop) of the amplifier circuit 90 is sufficiently small, power before and after the voltage conversion becomes equal, so that the amplifier circuit 90 can amplify the input current into a current having a current value of n times and output the current in this case.

As described above, according to the power supply unit 10 of the fourth modification, the current output from the power supply 12 can be amplified by the amplifier circuit 90, converted into the current having the large current value, and then input to the constant current circuit 70. As a result, even if the power supply 12 is not changed to another power supply that is capable of outputting a large current, the constant current value $I_H$ that can be output by the constant current circuit 70 can be increased, and the temperature resolution Res [° C.] can be increased. The amplifier circuit 90 may be provided on an upstream side of the first switch SW1 of the first circuit C11 instead of being provided between the power supply 12 and the heating and measurement circuit C1.

Figure 15:
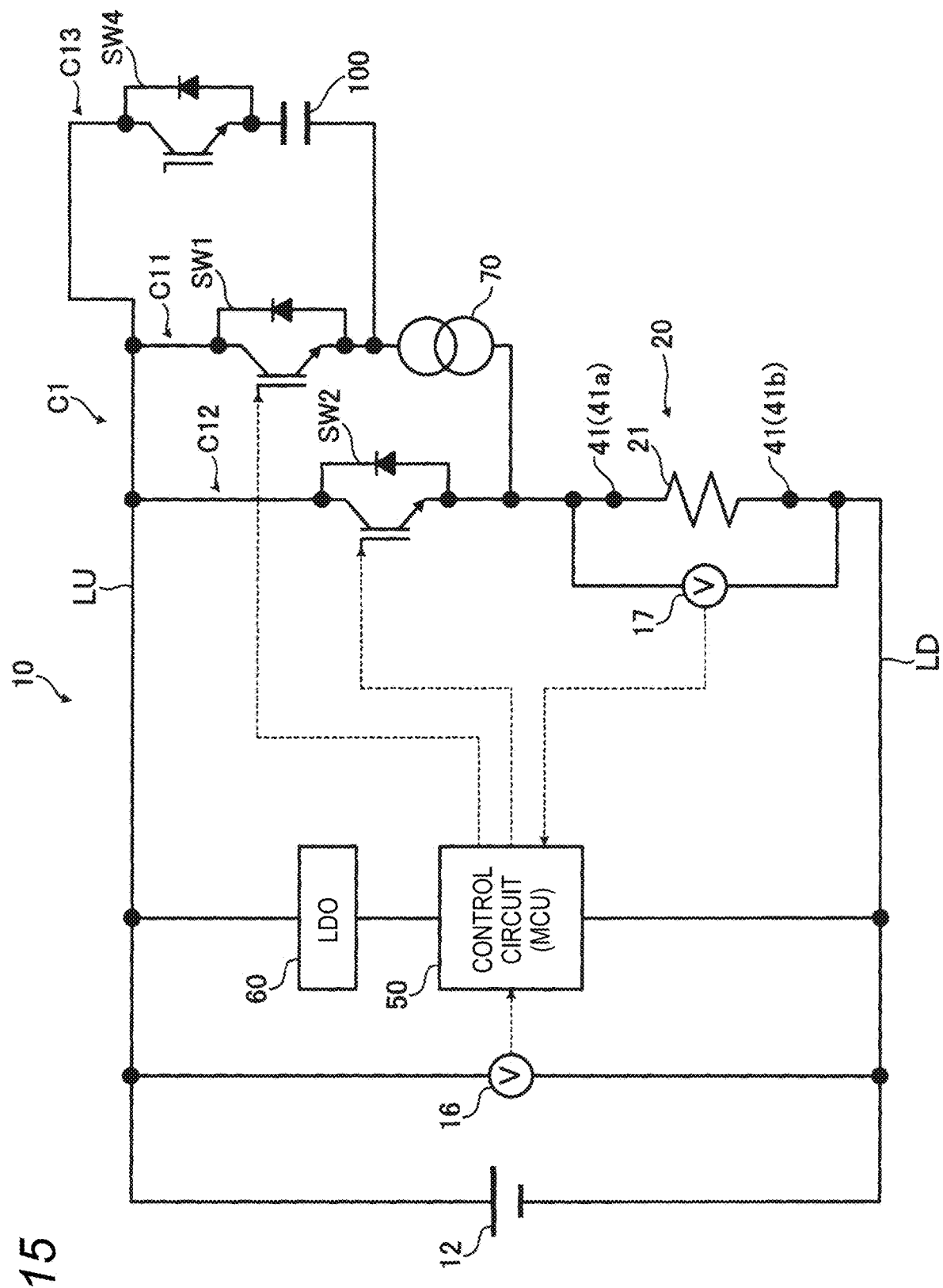
FIG. 15 is a second diagram illustrating the fourth modification of the power supply unit.

As another example for amplifying the current input to the constant current circuit 70, a configuration illustrated in FIG. 15 can also be considered. In the following description of FIG. 14, descriptions of the same portions as those in FIG. 11 will be omitted as appropriate.

In the example of FIG. 15, a third circuit C13 which includes a fourth switch SW4 and a capacitor 100 is connected in parallel to the first switch SW1 of the first circuit C11 in the heating and measurement circuit C1, which is different from the example described in FIG. 11. The control circuit 50 turns on the fourth switch SW4 at predetermined timing to store electricity in the capacitor 100.

In this way, when the first switch SW1 is turned on, a current from the side of the first switch SW1 and a current from the side of the third circuit C13 (that is, a current discharged from the capacitor 100) can be input to the constant current circuit 70. Therefore, it is possible to input a current having a larger current value than a current that can be output from the power supply 12 to the constant current circuit 70.

The control method described in the present embodiment can be implemented by executing a program prepared in advance by a computer (for example, an MCU). The control program is recorded in a computer-readable recording medium, such as a memory, and is executed by being read out from the recording medium by a computer. Moreover, the control program may be distributed via a network such as the Internet.

The present disclosure is not limited to the embodiment and the modifications described above, and modifications, improvements, and the like can be made as appropriate.

For example, although the control circuit 50 acquires both the electric resistance value $R_H$ and the temperature T of the load 21 in the above-described embodiment and modifications, the present disclosure is not limited thereto. The control circuit 50 may only acquire one of the electric resistance value $R_H$ and the temperature T of the load 21 (for example, the electric resistance value $R_H$).

That is, the scope of rights of the present disclosure includes a mode in which only one of the electric resistance value and the temperature of the load is acquired, and a mode in which both the electric resistance value and the temperature of the load are acquired.

Although the first cartridge 20 including the load 21 is detachably attached to the power supply unit 10 in the above-described embodiment and modifications, the first cartridge 20 including the load 21 may also be integrated with the power supply unit 10.

The present specification describes at least the following matters. It should be noted that although corresponding components in the above embodiment are shown in parentheses, the present disclosure is not limited thereto.

(1) A control device (the power supply unit 10) of an aerosol inhaler (the aerosol inhaler 1) including a load (the load 21) heating an aerosol generation source (the aerosol source 22, the flavor source 31), a temperature and an electric resistance value of the load being correlated, the control device includes:

a voltage sensor (the load voltage sensor 17) configured to output a voltage value applied to the load;

a constant current circuit (the constant current circuit 70) configured to output a constant current to the load; and a control circuit (the control circuit 50) configured to acquire the electric resistance value of the load or the temperature of the load based on output of the voltage sensor and the constant current.

According to (1), since the electric resistance value or the temperature of the load is acquired based on the output of the voltage sensor (that is, the voltage value applied to the load) and the constant current output to the load by the constant current circuit, the electric resistance value or the temperature of the load can be acquired with high accuracy with a simple configuration.

(2) The control device of the aerosol inhaler according to (1), in which the constant current is equal to or greater than 1 [A].

According to (2), since the constant current output to the load by the constant current circuit is equal to or greater than 1 [A], a certain degree of resolution (temperature resolution) can be secured for the temperature of the load that can be detected by the control circuit. For example, by setting the constant current output to the load by the constant current circuit to 1 [A] or more, it is possible to detect the temperature of the load with accuracy required for detecting detachment and attachment of the load with respect to the power supply.

(3) The control device of the aerosol inhaler according to (1), in which the constant current is equal to or greater than 2 [A].

According to (3), since the constant current output to the load by the constant current circuit is 2 [A] or more, the temperature resolution can be increased. For example, by setting the constant current output to the load by the constant current circuit to 2 [A] or more, it is possible to detect the temperature of the load with accuracy required for authentic product authentication of the load or detection of remaining amount of the aerosol source (for example, depletion detection).

(4) The control device of the aerosol inhaler according to (1), in which the constant current is equal to or greater than 3 [A].

According to (4), since the constant current output to the load by the constant current circuit is 3 [A] or more, the temperature resolution can be further increased. For example, by setting the constant current output to the load by the constant current circuit to 3 [A] or more, it is possible to further improve the accuracy of the authentic product authentication of the load or the detection of remaining amount of the aerosol source (for example, the depletion detection) performed based on the detected temperature of the load.

(5) The control device of the aerosol inhaler according to any one of (2) to (4), in which the control circuit includes an analog-digital converter (the analog-digital converter 57) to which the output of the voltage sensor is input, and the analog-digital converter is configured such that the output of the voltage sensor is input without being amplified.

According to (5), since the output of the voltage sensor is input to the analog-digital converter without being amplified, noise included in the output of the voltage sensor can be prevented from being amplified, and accuracy of the temperature of the load acquired based on the output can be improved.

(6) The control device of the aerosol inhaler according to (1), in which the constant current is less than 1 [A], the control circuit includes an analog-digital converter (the analog-digital converter 57) to which the output of the voltage sensor is input, and the analog-digital converter is configured such that the output of the voltage sensor is amplified and input.

According to (6), since the constant current is less than 1 [A], Joule heat generated by the constant current can be reduced when the electric resistance value or the temperature of the load is acquired, so that an influence of energization on the electric resistance value or the temperature of the load can be reduced. Moreover, by amplifying the output of the voltage sensor, even when the current value of the constant current is reduced, detection accuracy of the electric resistance value or the temperature of the load can be maintained.

(7) The control device of the aerosol inhaler according to (6), in which the constant current is equal to or less than 100 [mA].

According to (7), since the constant current is less than 100 [mA], the Joule heat generated by the constant current can be further reduced when the electric resistance value or the temperature of the load is acquired, so that the influence of the energization on the electric resistance value or the temperature of the load can be further reduced.

(7) The control device of the aerosol inhaler according to (1) further includes:

an amplifier circuit (the amplifier circuit 90, the third circuit C13) configured to amplify a current input to the constant current circuit.

According to (8), since the amplifier circuit for amplifying the current input to the constant current circuit is provided, the current value of the constant current output to the load by the constant current circuit can be increased without changing the power supply. As a result, the detection accuracy of the temperature of the load can be improved without changing the power supply.

(9) The control device of the aerosol inhaler according to (8), in which the amplifier circuit is a switching regulator capable of decreasing an input voltage.

According to (9), it is possible to reduce loss when amplifying the current input to the constant current circuit, and to reduce power consumption when the electric resistance value or the temperature of the load is acquired.

(10) The control device of the aerosol inhaler according to any one of (1) to (9) further includes:

a first circuit (the first circuit C11) which includes the constant current circuit and a first switch (the first switch SW1); and a second circuit (the second circuit C12) which is connected in parallel with the first circuit and includes a second switch (the second switch SW2).

According to (10), the second circuit which is connected in parallel with the first circuit and includes the second switch is provided, so it is possible to input a current to the load via the second circuit. That is, it is possible to input a current that is not restricted by the constant current circuit of the first circuit to the load, and it is possible to efficiently heat the aerosol source by the load.

(11) The control device of the aerosol inhaler according to any one of (1) to (10) further includes:

a connector (the discharge terminal 41) capable of attaching and detaching the load; and a resistor (the shunt resistor 80) connected in parallel with the connector, in which the voltage sensor outputs a voltage value applied to the resistor when the load is not attached to the connector.

According to (11), since the voltage sensor outputs the voltage value applied to the resistor when the load is not attached to the connector, it is possible to easily determine whether the load is attached to the connector based on the output of the voltage sensor.

(12) The control device of the aerosol inhaler according to (11), in which an electric resistance value of the resistor is higher than an electric resistance value of the load.

According to (12), since the electric resistance value of the resistor is higher than the electric resistance value of the load, a current passing through the resistor when the load is attached to the connector can be reduced, and power consumption for determining whether the load is attached to the connector based on the output of the voltage sensor can be reduced.

(13) A control method of an aerosol inhaler (the aerosol inhaler 1) including a load (the load 21) heating an aerosol generation source (the aerosol source 22, the flavor source 31), a temperature and an electric resistance value of the load being correlated, the control method includes:

first acquiring (step S03) a voltage value applied to the load; and second acquiring (step S04) the electric resistance value of the load or the temperature of the load based on the voltage value applied to the load acquired in the first acquiring and a current value of a constant current output to the load.

According to (13), since the electric resistance value or the temperature of the load is acquired based on the output of the voltage sensor (that is, the voltage value applied to the load) and the constant current output to the load by the constant current circuit, the electric resistance value or the temperature of the load can be acquired with high accuracy with a simple configuration.

(14) A control device (the power supply unit 10) of an aerosol inhaler (the aerosol inhaler 1) including a load (the load 21) heating an aerosol generation source (the aerosol source 22, the flavor source 31), a temperature and an electric resistance value of the load being correlated, the control device includes:

a sensor (the load voltage sensor 17) configured to output an electric variable of the load; and a control circuit (the control circuit 50) configured to acquire the electric resistance value of the load or the temperature of the load based only on output of the sensor and a constant.

According to (14), since the electric resistance value or the temperature of the load is acquired based only on the output of the voltage sensor (that is, the electric variable of the load) and the constant, the electric resistance value or the temperature of the load can be acquired with high accuracy with a simple configuration.

(15) A control method of an aerosol inhaler (the aerosol inhaler 1) including a load (the load 21) heating an aerosol generation source (the aerosol source 22, the flavor source 31), a temperature and an electric resistance value of the load being correlated, the control method includes:

first acquiring (step S03) an electric variable of the load; and second acquiring (step S04) the electric resistance value of the load or the temperature of the load based only on the electric variable of the load acquired in the first acquiring and a constant.

According to (15), since the electric resistance value or the temperature of the load is acquired based only on the electric variable of the load and the constant, the electric resistance value or the temperature of the load can be acquired with high accuracy with a simple configuration.

(16) A control program configured to cause a computer (the control circuit 50, the processor 55) to execute the control method according to (13) or (15).

According to (16), since the electric resistance value or the temperature of the load is acquired based only on the electric variable of the load and the constant, the electric resistance value or the temperature of the load can be acquired with high accuracy with a simple configuration.

What is claimed is:

1. A control device of an aerosol inhaler including a load heating an aerosol generation source, a temperature and an electric resistance value of the load being correlated, the control device comprising:

a voltage sensor configured to output a voltage value applied to the load;

a constant current circuit configured to output a constant current to the load;

a control circuit configured to acquire the electric resistance value of the load or the temperature of the load based on output of the voltage sensor and the constant current;

a switching regulator configured to decrease an input voltage to amplify a current input from a power supply to the constant current circuit; and an amplifier circuit voltage sensor configured to detect an output voltage from the switching regulator and send information indicating the detected output voltage to the control circuit.

2. The control device of the aerosol inhaler according to claim 1, wherein the constant current is equal to or greater than 1 [A].

3. The control device of the aerosol inhaler according to claim 1, wherein the constant current is equal to or greater than 2 [A].

4. The control device of the aerosol inhaler according to claim 1, wherein the constant current is equal to or greater than 3 [A].

5. The control device of the aerosol inhaler according to claim 2, wherein the control circuit includes an analog-digital converter to which the output of the voltage sensor is input, and the analog-digital converter is configured such that the output of the voltage sensor is input without being amplified.

* * * * *